United States Patent [19]

Shinjo et al.

[11] Patent Number: 5,034,151
[45] Date of Patent: Jul. 23, 1991

[54] MESOMORPHIC COMPOUND, FERROELECTRIC LIQUID CRYSTAL COMPOSITION CONTAINING SAME AND FERROELECTRIC LIQUID CRYSTAL DEVICE

[75] Inventors: Kenji Shinjo, Atsugi; Akio Yoshida, Chigasaki; Takashi Iwaki, Isehara; Takao Takiguchi, Tokyo; Hiroyuki Kitayama, Sagamihara; Kazuharu Katagiri, Tama, all of Japan

[73] Assignee: Canon Kabushiki Kaisha, Tokyo, Japan

[21] Appl. No.: 329,316

[22] Filed: Mar. 27, 1989

[30] Foreign Application Priority Data

Mar. 28, 1988 [JP] Japan .................................. 63-75078
Jun. 24, 1988 [JP] Japan .................................. 63-157675
Mar. 15, 1989 [JP] Japan .................................. 1-64775

[51] Int. Cl.$^5$ .................... C09K 19/34; C07D 271/10; C07D 271/12; C07D 413/00
[52] U.S. Cl. ........................ 252/299.61; 252/299.01; 350/350 R; 350/350 S; 548/143; 548/144; 548/145; 548/136
[58] Field of Search ...................... 252/299.61, 299.01; 350/350 R, 350 S; 548/136, 143, 144, 145

[56] References Cited

U.S. PATENT DOCUMENTS

| 4,020,080 | 4/1977 | Irick et al. ........................ 548/143 X |
| 4,667,020 | 5/1987 | Etzbach et al. ............ 252/299.61 X |

FOREIGN PATENT DOCUMENTS

| 3515373 | 11/1986 | Fed. Rep. of Germany ........................ 252/299.61 |
| 3801799 | 9/1988 | Fed. Rep. of Germany ........................ 252/299.61 |
| 3819972 | 1/1989 | Fed. Rep. of Germany ........................ 252/299.61 |
| 2617496 | 6/1988 | France ............................ 252/299.61 |
| 117014 | 12/1985 | German Democratic Rep. .................. 252/299.61 |
| 240385 | 10/1986 | German Democratic Rep. .................. 252/299.61 |
| 240386 | 10/1986 | German Democratic Rep. .................. 252/299.61 |
| 247221 | 7/1987 | German Democratic Rep. .................. 252/299.61 |
| 247694 | 7/1987 | German Democratic Rep. .................. 252/299.61 |
| 245142 | of 1986 | Japan ............................. 252/299.61 |
| 246722 | of 1986 | Japan ............................. 252/299.61 |
| 246723 | of 1986 | Japan ............................. 252/299.61 |
| 246724 | of 1986 | Japan ............................. 252/299.61 |
| 249024 | of 1986 | Japan ............................. 252/299.61 |
| 249025 | of 1986 | Japan ............................. 252/299.61 |
| 08019 | 10/1988 | PCT Int'l Appl. ............ 252/299.61 |
| 8808019 | 10/1988 | World Int. Prop. O. ....... 252/299.61 |

OTHER PUBLICATIONS

Dimitrowa, K., et al., J. Prakt. Chemie, vol. 322, No. 6, pp. 933-944, (1980).
Demus, D., et al., Flussige Kristalle in Tabellen II, VEB Deutscher Verlag fur Grundstoffindustrie, Leipzig, pp. 359-361, (1984).
Gray, G. W., et al., Liquid Crystals & Plastic Crystals, vol. 1, Ellis Horwood, Ltd., Chichester, UK, pp. 142-143, (1974).

Primary Examiner—John S. Maples
Assistant Examiner—Richard Treanor
Attorney, Agent, or Firm—Fitzpatrick, Cella, Harper & Scinto

[57] ABSTRACT

There is disclosed a mesomorphic compound represented by the following formula (I):

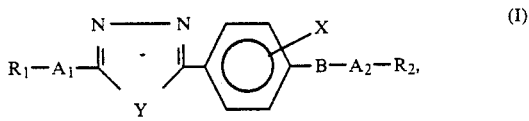

wherein $A_1$ denotes a single bond, (Abstract continued on next page.)

denotes

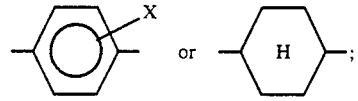

X denotes hydrogen, a halogen or cyano group; Y denotes oxygen or sulfur; $R_1$ and $R_2$ respectively denotes a linear or branched alkyl, alkoxy, alkylcarbonyloxy, alkoxycarbonyl or alkoxycarbonyloxy group each having 1-18 carbon atoms and each capable of having a substituted of chloro, bromo, cyano, alkoxy or akoxycarbonyl group; and B denotes

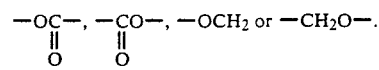

A ferroelectric liquid crystal composition comprises at least two mesomorphic compounds including at least one mesomorphic compound represented by the formula (I). A ferroelectric liquid crystal device is constituted by disposing the ferroelectric liquid crystal composition between a pair of substrates.

10 Claims, 1 Drawing Sheet

MESOMORPHIC COMPOUND, FERROELECTRIC LIQUID CRYSTAL COMPOSITION CONTAINING SAME AND FERROELECTRIC LIQUID CRYSTAL DEVICE

FIELD OF THE INVENTION AND RELATED ART

The present invention relates to a mesomorphic compound having an oxidiazole or thiadiazole ring, a ferroelectric liquid crystal composition containing the mesomorphic compound and a ferroelectric liquid crystal device using the composition.

Clark and Lagerwall proposed a ferroelectric liquid crystal display system, called an SSFLC (Surface Stabilized Ferroelectric Liquid Crystal) System in 1980. The SSFLC system is principally characterized in release of a helical structure (having a pitch of 1 0) owned by a ferroelectric liquid crystal (hereinafter sometimes abbreviated as "FLC") by utilizing the boundary effect of a pair of substrate surfaces, more specifically through the following features.

(1) The spacing (cell gap) between the pair of substrates is set to a sufficiently small value to release the above-mentioned helical structure.

(2) The liquid crystal molecules are set to align in parallel with the boundaries with the substrates, whereby the smectic layers of FLC are disposed perpendicularly to the substrates.

(3) Further, the direction of the alignment of liquid crystal molecules in contact with at least one of the substrates is regulated, whereby the direction of the smectic layers is uniformized over the entire cell area.

When the alignment state formed through such stepwise molecular control is viewed macroscopically, stable longer-axis directions (director n) of ferroelectric liquid crystal molecules are restricted to two directions. In an FLC display, the fact that the two directions (average directions of n) are discriminatable by means of a polarizer is utilized for display.

The basic mechanism of switching between the above-mentioned two stable directions is based on the utilization of a ferroelectricity which FLC shows in its smectic C* phase. FLC has a molecular dipole moment (RAR/u/) in a plane parallel to the smectic layer and is present between the cell substrates in such a form that it is disposed continuously while changing the direction of the dipole moment (RAR/u/) to some extent to provide an average spontaneous polarization (Ps) in a direction from the lower substrate to the upper substrate or in the reverse direction. Each of the directions (upward and downward) of the spontaneous polarization (Ps) corresponds to either one of the above-mentioned molecular longer axes (n), so that switching by electric fields becomes possible.

More specifically, when an electric field is applied to the FLC layer from outside, the dipole moments (n) in the layer are all uniformly oriented (U1) in the direction of the electric field, and when the electric field is removed, the dipole moments are settled at a state (S1) after some relaxation time (on the order of 1 μs-2 ms varying depending on an FLC used). U1 is a uniform state having a higher degree of order and optically a better uniaxial characteristic than S1, and S2 is a twisted state where the dipoles of FLC are somewhat twisted to provide a lower uniaxial characteristic than U1 but the directions of the spontaneous polarizations are uniform. Similarly, when the polarity of the external electric field is reversed, there are formed states U2 and S2. As a result, it is possible to select U1 or U2 (and thus S1 or S2) by the polarity of the electric field applied. This is referred to as bistability.

In addition to the above-described characteristic of showing bistability, the ferroelectric liquid crystal has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc.

Among a response time $\tau$, the magnitude of spontaneous polarization Ps and viscosity $\eta$, the following relationship exists: $\tau = \eta/(Ps \cdot E)$, where E is an applied voltage. Accordingly, a large response speed can be obtained by (a) increasing the spontaneous polarization, (b) lowering the viscosity $\tau$, or (c) increasing the applied voltage. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that a remarkable increase in response speed may not be attained as a result.

Further, if it is assumed that the operation temperature of an actual display device is 5–40° C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

In a representative FLC cell structure, a pair of substrates are disposed, each substrate of e.g. glass being provided with an electrode pattern of e.g. ITO, further thereon with a layer of e.g. $SiO_2$ (about 1000 Å) for preventing short circuit between the pair of substrates and further thereon with a film of e.g. polyimide (PI; such as SP-510, 710, ... available from Toray K.K.) of about 500 Å in thickness, which is then treated for alignment control by rubbing with e.g. an acetate fiberplanted cloth. Such a pair of substrates are disposed opposite to each other so that their alignment control directions are symmetrical and the spacing between the substrates is held at 1–3 microns.

On the other hand, it is known that the FLC molecules aligned under such conditions are disposed in succession so that their directors n are twisted between the substrates and do not show a uniaxial alignment or orientation (S1, S2 mentioned above). A problem in this case is a low transmittance through the liquid crystal layer.

The optical selection between the two stable states is effected by disposing a pair of polarizers in cross nicols between which the above cell is interposed, and when the absorption axis of the polarizers is disposed in alignment with the average molecular axis of either one of S1 and S2, e.g. S1, the resultant transmittance becomes extremely low to display "black". Then, when the molecular position is switched to the S2 state, the molecular position is deviated from the absorption axis of the polarizers by $2\theta a$ which is an angle between S1 and S2, so that transmission of light is caused to display "white".

The transmitted light intensity I is given by the following equation with respect to the incident light intensity $I_0$ under cross nicols when the uniaxial alignment of the molecules is assumed:

$$I = I_0 \sin^2(4\theta a) \cdot \sin^2(\pi \Delta n d/\lambda) \quad \ldots (1),$$

wherein $\Delta n$ denotes the refractive index anisotropy of the FLC; d, the cell thickness; and $\lambda$, the wavelength of the incident light.

When the above-mentioned cell is used, it has been experimentally known that $\theta a$ is 5–8 degrees under a twisted alignment condition and is little affected by a liquid crystal material used.

The control of physical properties affecting the term $\Delta n \pi/\lambda$ cannot be easily performed, so that it is desired to increase $\theta a$ to increase Ia. However, this has not been successfully accomplished by only a static alignment technique.

With respect to such a problem, it has been proposed to utilize a torque relating to a dielectric anisotropy $\Delta \epsilon$ of an FLC (1983 SID report from AT & T; Japanese Laid-Open Patent Appln. Nos. 245142/1986, 246722/1986, 246723/1986, 246724/1986, 249024/1986 and 249025/1986). More specifically, an effective value of AC electric field is applied in a period other than switching so that the molecular stable states are shifted from S1 and S2 under the electric field due to the generation of a dielectric polarization (AC stabilization effect). A torque $\Gamma$Ps acting on FLC molecules involved in switching of states and a torque $\Gamma \Delta \epsilon$ acting on FLC molecules relating to the AC stabilization effect are respectively proportional to physical properties as shown in the following formulas:

$$\Gamma Ps \propto Ps \cdot E \quad \ldots (2)$$

$$\Gamma \Delta \epsilon \propto \tfrac{1}{2} \Delta \epsilon \cdot \epsilon_0 \cdot E^2 \quad \ldots (3)$$

The above formula (3) apparently shows that the sign and absolute value of $\Delta \epsilon$ of the FLC play an important role.

The sole figure attached hereto shows the change of $\theta a$ versus Vrms experimentally measured for for 4 FLC's having different values of $\Delta \epsilon$. The measurement was conducted under application of AC rectangular pulses of 60 KHz so as to remove the influence of Ps.

The curves (I)–(IV) correspond to the results obtained by using FLCs showing the following $\Delta \epsilon$ values.

$$\Delta \epsilon \simeq -5.5, \quad (I)$$

$$\Delta \epsilon \simeq -3.0, \quad (II)$$

$$\Delta \epsilon \simeq -0, \quad (III)$$

$$\Delta \epsilon \simeq 1.0. \quad (IV)$$

Qualitatively, the order of $\Delta \epsilon$ was (I)<(II)<(III)<(IV).

As is clear from the graph in the figure, a larger negative value of $\Delta \epsilon$ provides a large $\theta a$ at a lower voltage and thus contributes to provision of an increased I.

The transmittances obtained by using the liquid crystals (I) and (III) were 15 % for (I) and 6 % for (III), thus showing a clear difference.

As is known from the above examples, the display characteristics of an SSFLC can be remarkably changed by controlling the properties relating to $\Delta \epsilon$ and Ps ($\eta$).

However, most of ferroelectric liquid crystal compositions used heretofore have a $\Delta \epsilon$ of nearly 0, so that an improvement in display characteristics through the above-mentioned AC stabilization effect can hardly be expected.

SUMMARY OF THE INVENTION

An object in general of the present invention is to solve the above-mentioned problems to provide a practical ferroelectric liquid crystal device.

A specific object of the present invention is to provide a liquid crystal composition and a liquid crystal device using the composition showing excellent response characteristics through utilization of a novel mesomorphic compound.

Another specific object of the present invention is to provide a liquid crystal composition and a liquid crystal device using the composition having remarkably improved display characteristics through utilization of a novel mesomorphic compound providing an AC stabilization effect.

According to the present invention, there is provided a mesomorphic compound represented by the following formula (I):

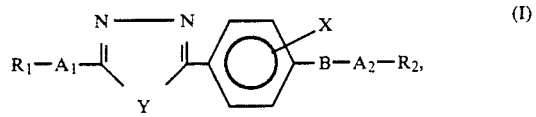

wherein $A_1$ denotes a single bond,

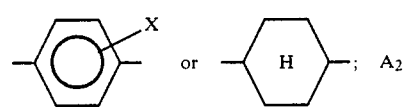

denotes

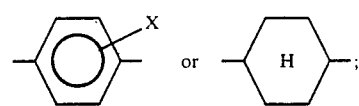

X denotes hydrogen, a halogen or cyano group; Y denotes oxygen or sulfur; $R_1$ and $R_2$ respectively denotes a linear or branched alkyl, alkoxy, alkylcarbonyloxy, alkoxycarbonyl or alkoxycarbonyloxy group each having 1-18 carbon atoms and each capable of having a substituted of chloro, bromo, cyano, alkoxy or alkoxycarbonyl group; and B denotes

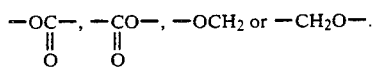

The present invention further provides a ferroelectric liquid crystal composition comprising at least two mesomorphic compounds, at least one of which is represented by the above formula (I), and a ferroelectric liquid crystal device comprising such a ferroelectric liquid crystal composition disposed between a pair of substrates.

The mesomorphic compound of the above formula (I) is characterized by having a unique π-electron-structure having hetero-atoms in its cyclic skeleton and an increased dielectric anisotropy in the direction of its shorter axis. According to our study, it has been found that a ferroelectic liquid crystal composition obtained by mixing such a mesomorphic compound with at least one other mesomorphic compound, particularly ferroelectric mesomorphic compound, or a ferroelectric liquid crystal device using such a ferroelectric liquid crystal composition, shows excellent response characteristics and also an AC stabilization effect to be provided with good display characteristics.

BRIEF DESCRIPTION OF THE DRAWINGS

The sole figure in the drawing shows changes in tilt angle θa versus effective voltage Vrms with respect to several ferroelectric liquid crystals having different values of dielectric anisotropy Δε.

DETAILED DESCRIPTION OF THE INVENTION (A) Among the mesomorphic compounds represented by the above general formula (I), those corresponding to the case of B being

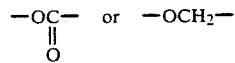

may be
synthesized through the following reaction steps; Formula (I)

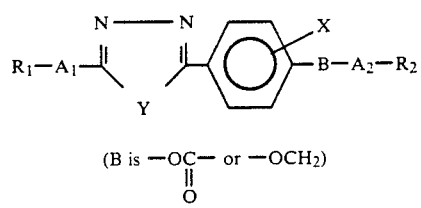

Step 1

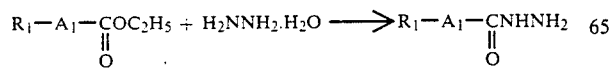

Step 2

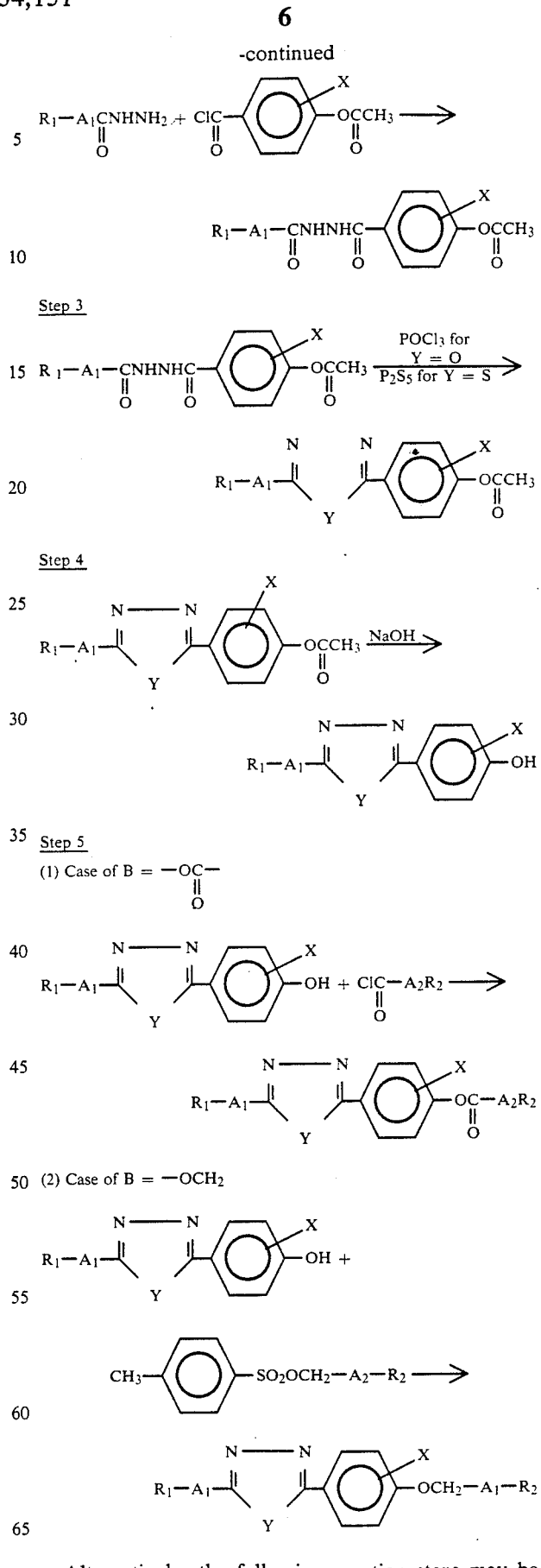

Alternatively, the following reaction steps may be applicable.

Step 1
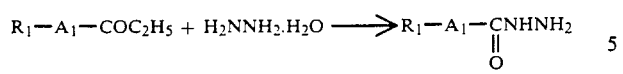
Step 2
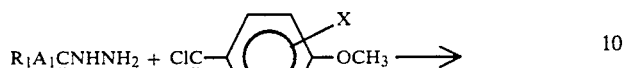
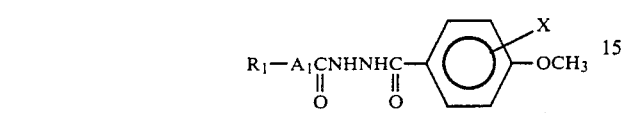
Step 3
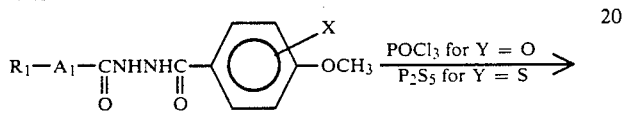
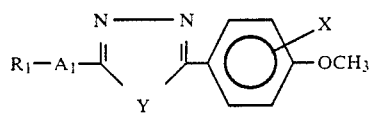
Step 4
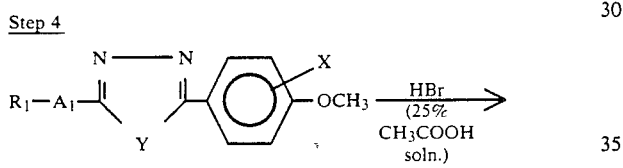
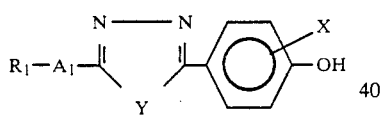
Step 5
(1) Case of B = —OC—
            ‖
            O
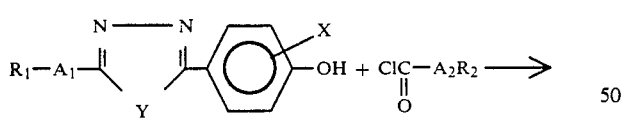
(2) Case of B = —OCH$_2$
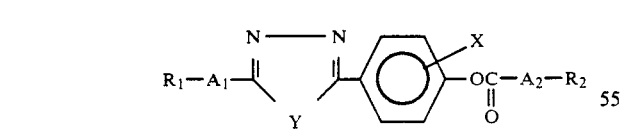
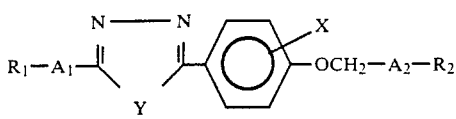
(B) The mesomorphic compounds corresponding to the case of B being
—CO—
‖
O
may be synthesized through the following reaction steps.
Formula (Ib)
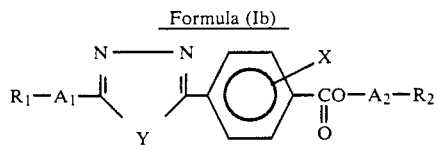
Step 2
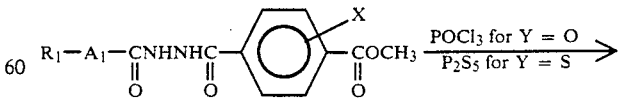
Step 3
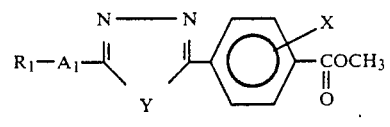
Step 4

-continued
Formula (Ib)
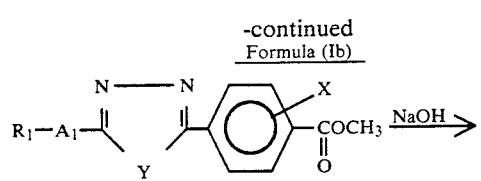
Step 5
-continued
Formula (Ib)
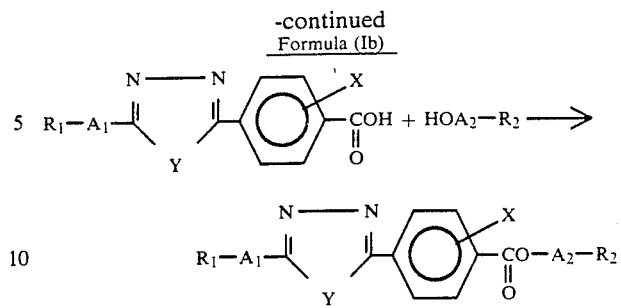
(C) The mesomorphic compounds corresponding to the case of B being —$CH_2O$— may be synthesized through the following reaction steps.
Formula (Ic)
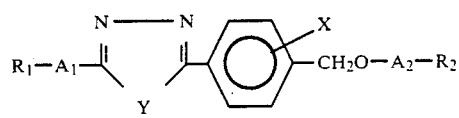
Step 2
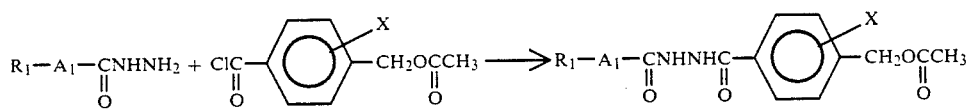
Step 3
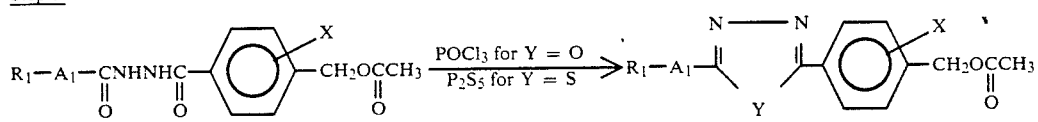
Step 4
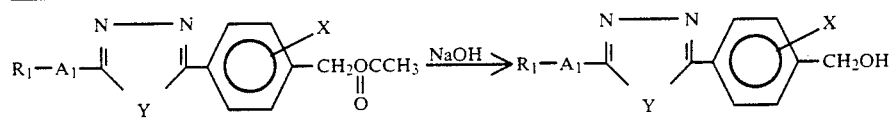
Step 5
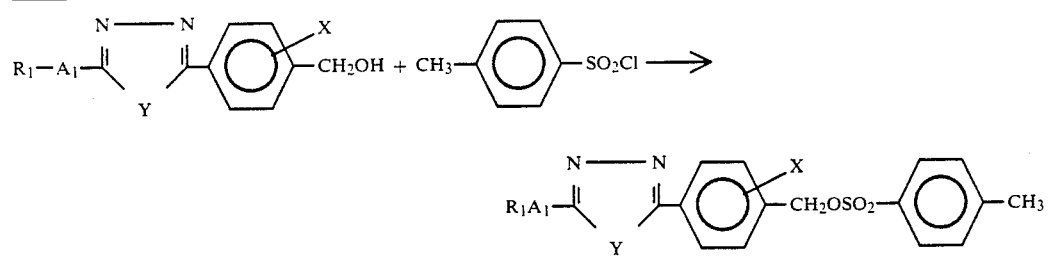
Step 6
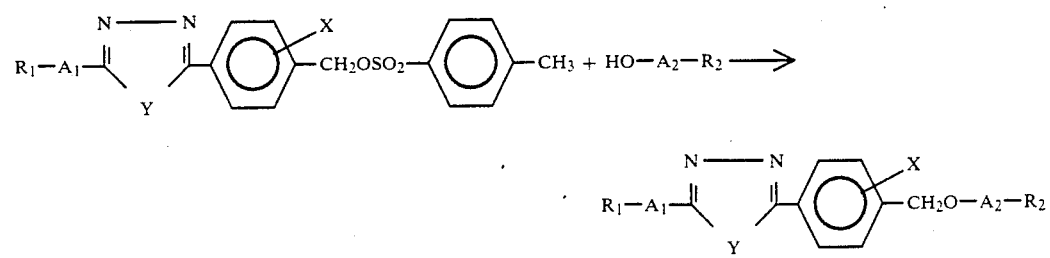
Specific examples of the mesomorphic compounds represented by the formula (I) are shown below.

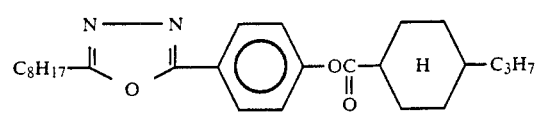 A-1
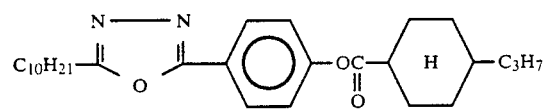 A-2
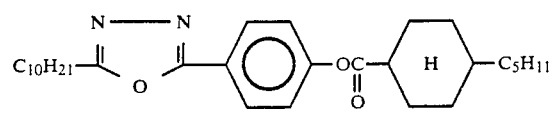 A-3
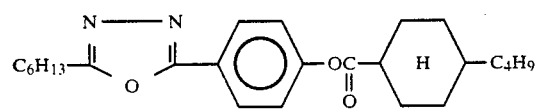 A-4
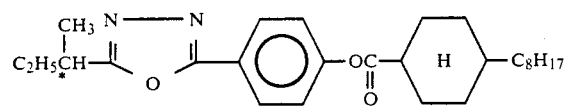 A-5
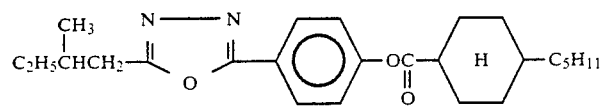 A-6
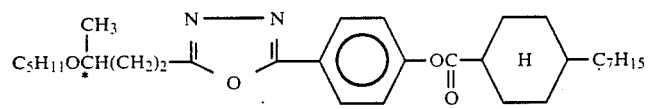 A-7
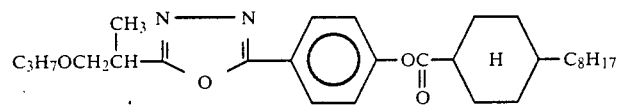 A-8
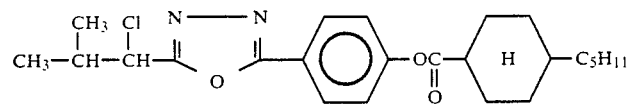 A-9
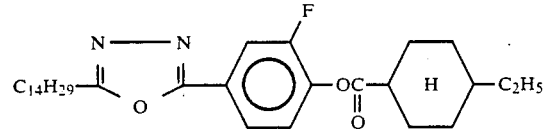 A-10
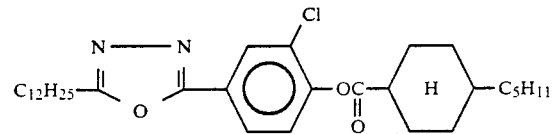 A-11
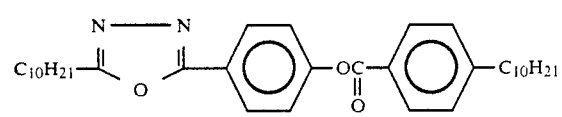 A-12
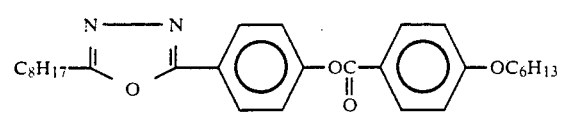 A-13

-continued
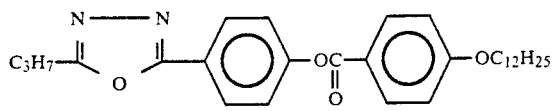 A-14
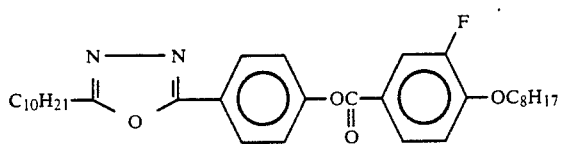 A-15
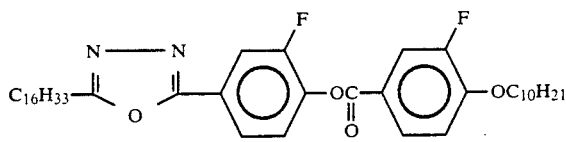 A-16
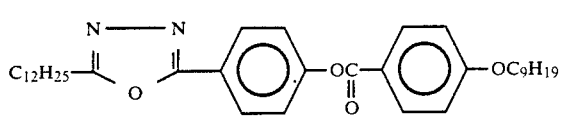 A-17
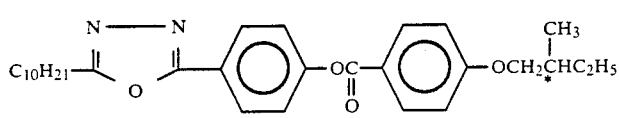 A-18
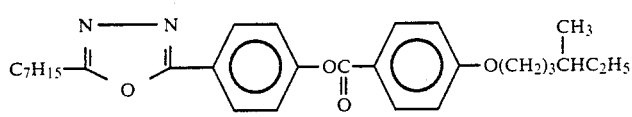 A-19
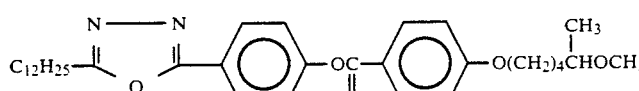 A-20
 A-21
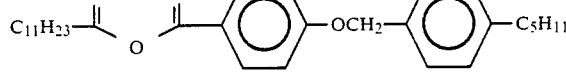 A-22
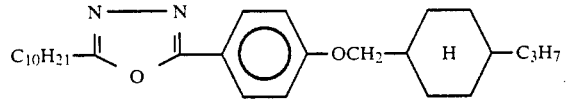 A-23
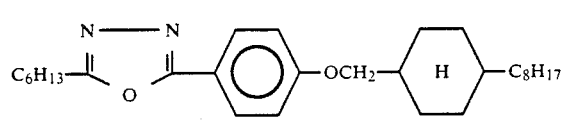 A-24
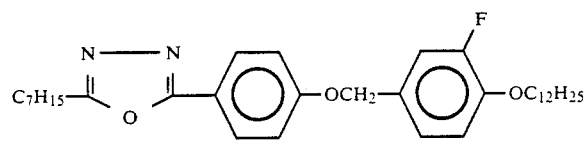 A-25
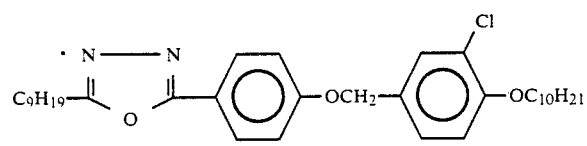 A-26
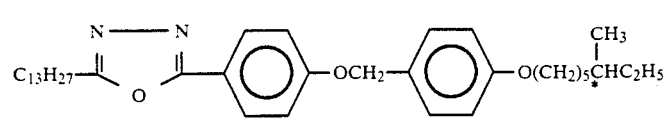

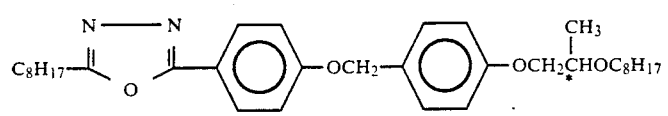
A-27
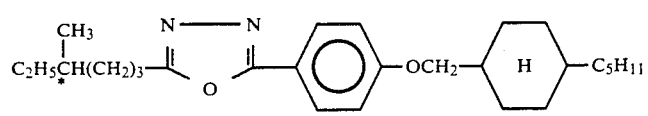
A-28
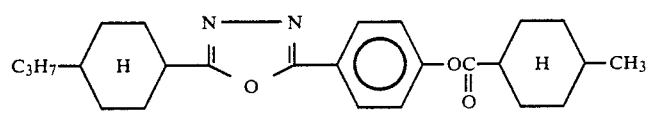
A-29
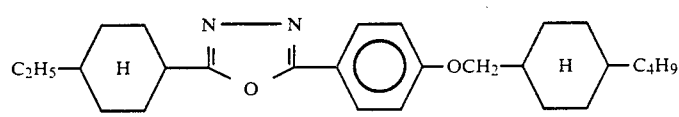
A-30
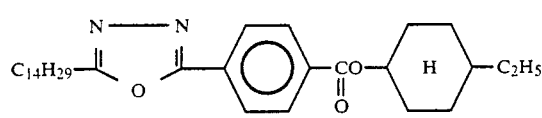
A-31
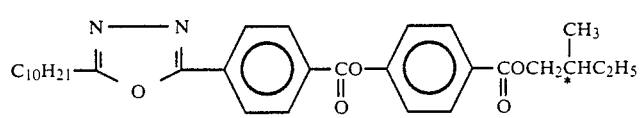
A-32
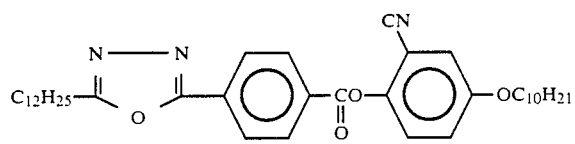
A-33
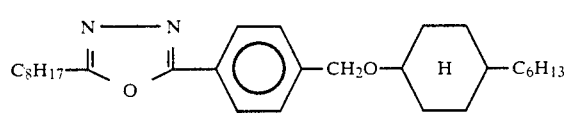
A-34
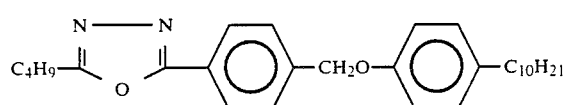
A-35
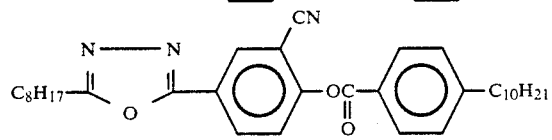
A-36
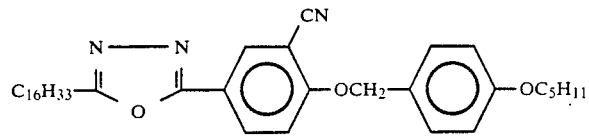
A-37
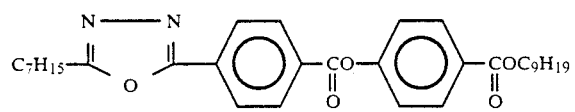
A-38
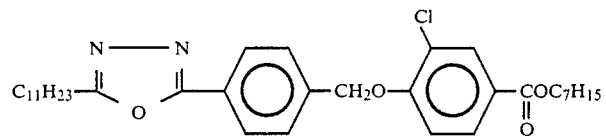
A-39

-continued
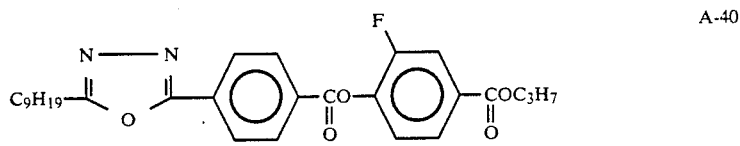
A-40
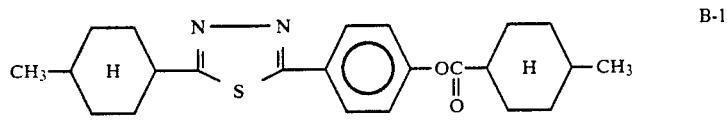
B-1
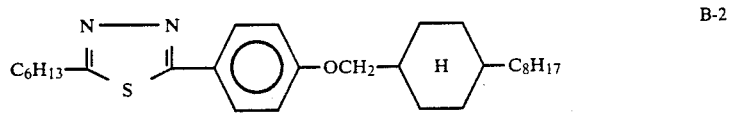
B-2
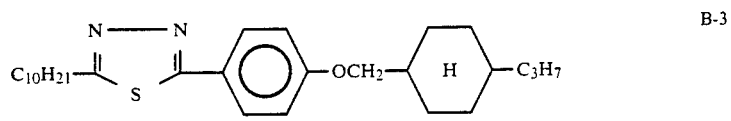
B-3
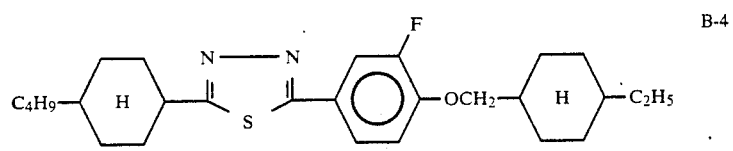
B-4
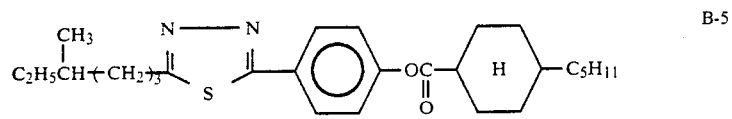
B-5
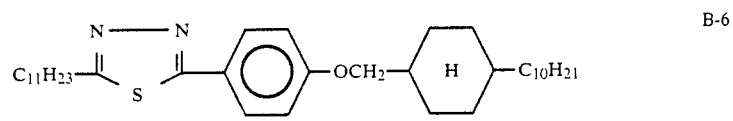
B-6
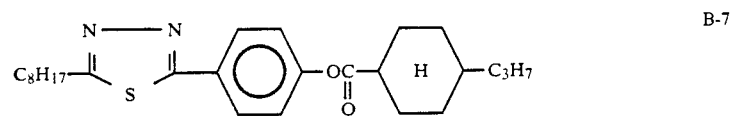
B-7
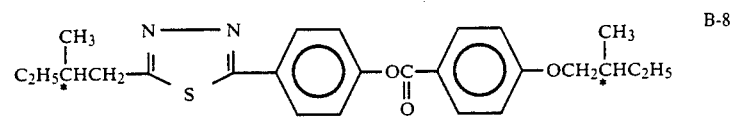
B-8
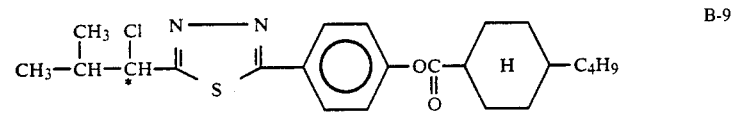
B-9
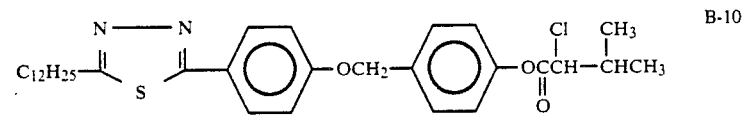
B-10
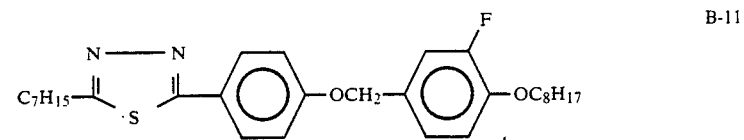
B-11

B-12
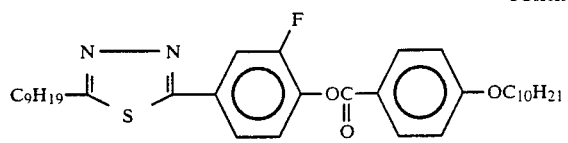
B-13
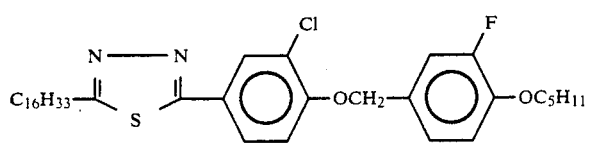
B-14
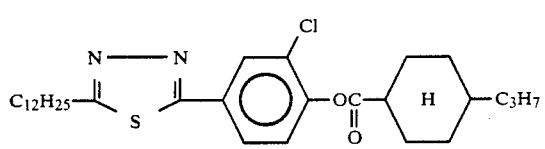
B-15
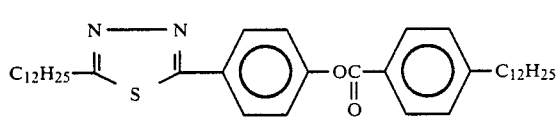
B-16
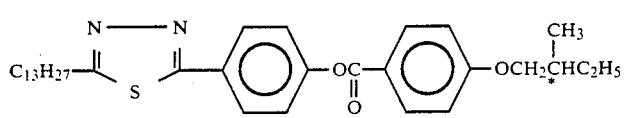
B-17
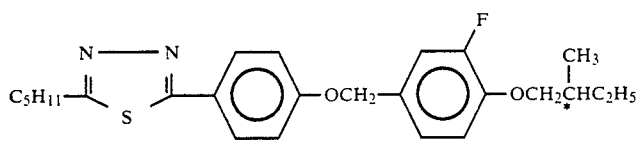
B-18
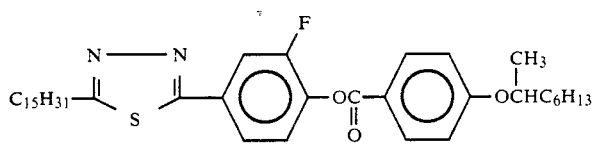
B-19
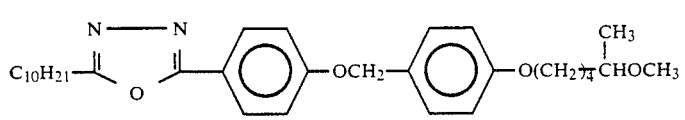
B-20
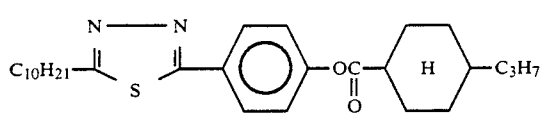
B-21
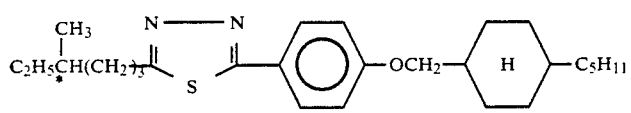
B-22
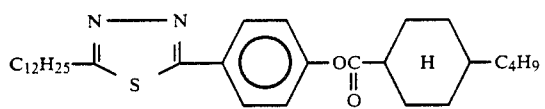
B-23
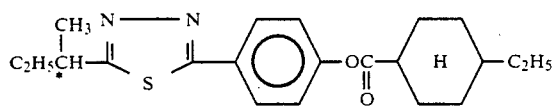
B-24
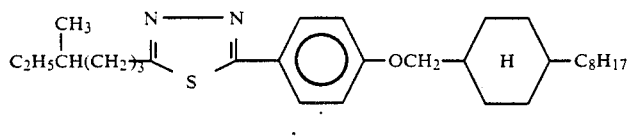

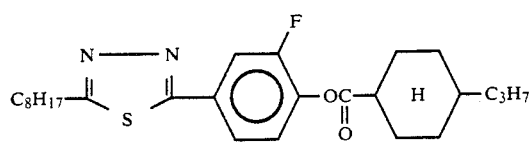 B-25
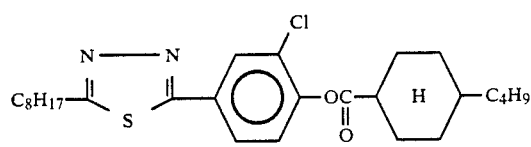 B-26
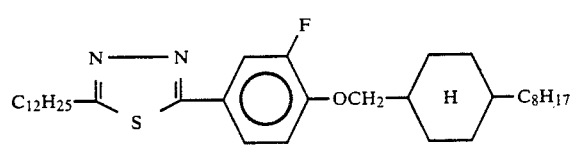 B-27
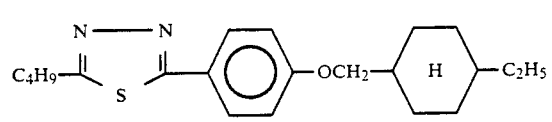 B-28
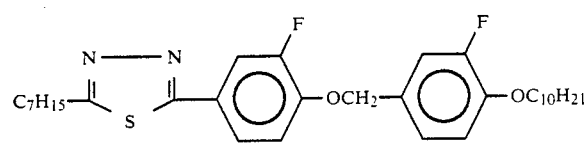 B-29
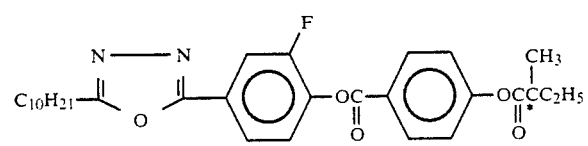 B-30
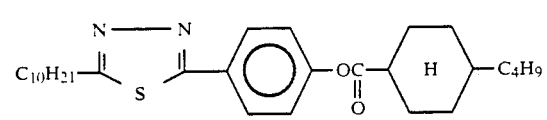 B-31
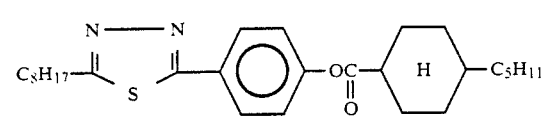 B-32
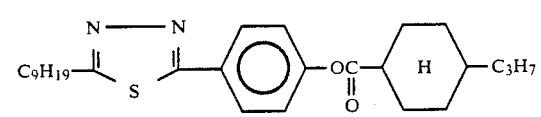 B-33
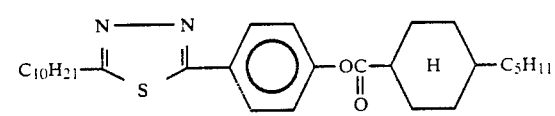 B-34
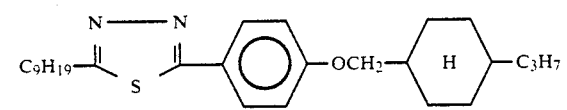 B-35
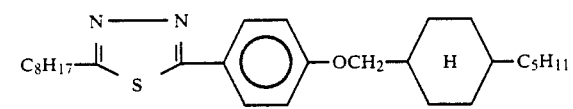 B-36

-continued
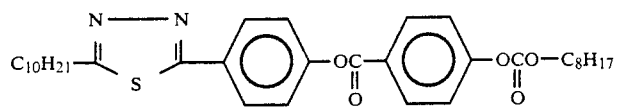 B-37
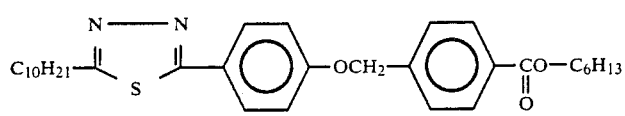 B-38
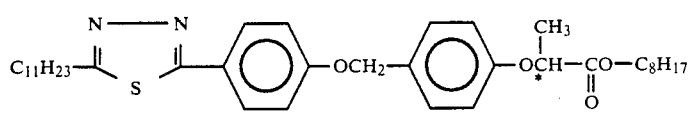 B-39
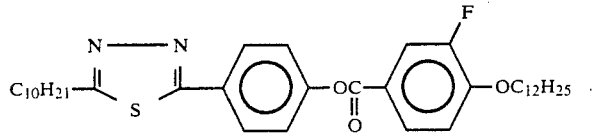 B-40
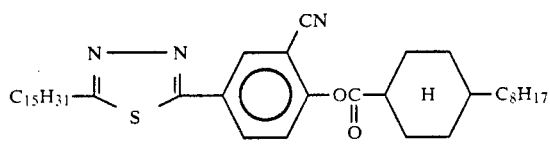 B-41
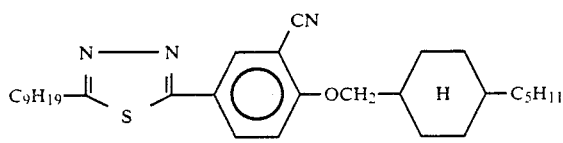 B-42
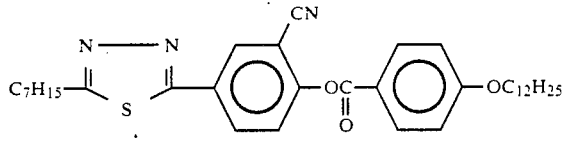 B-43
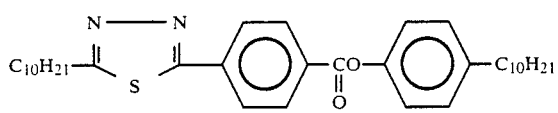 B-44
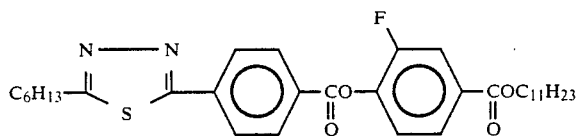 B-45
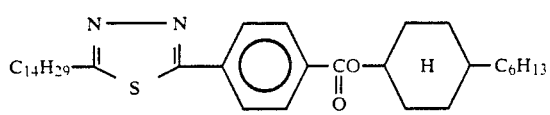 B-46
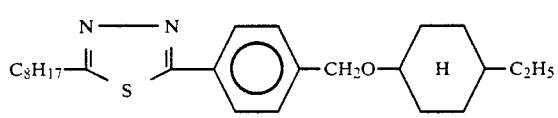 B-47
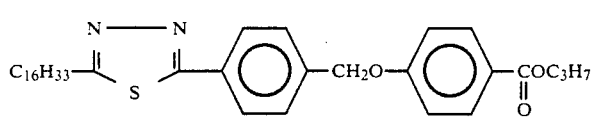 B-48

-continued

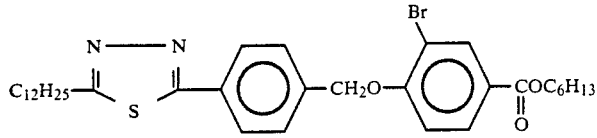
B-49

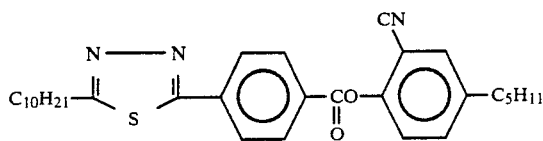
B-50

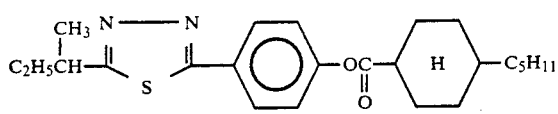
B-51

The liquid crystal composition of the present invention comprises at least two mesomorphic compound, at least one of which is represented by the formula (I) as described above. More specifically, the liquid crystal composition according to the present invention comprises, in addition to the mesomorphic compound represented by the above formula (I), another compound, particularly mesomorphic compound, selected from the classes of compounds as described below in order to control various properties of the composition, such as spontaneous polarization, helical pitch, phase transition series and related phase temperature ranges, response characteristics, tilt angle, and dielectric anisotropy.

In this instance, it is desirable that the mesomorphic compound represented by the formula (I) is used to constitute 0.5–60 wt. %, preferably 5–40 wt. %, of the resultant liquid crystal composition.

Class A: Optically active compounds yielding a helix when added to a non-chiral nematic phase.

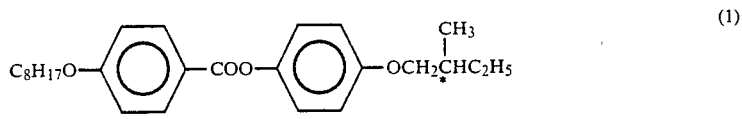
(1)

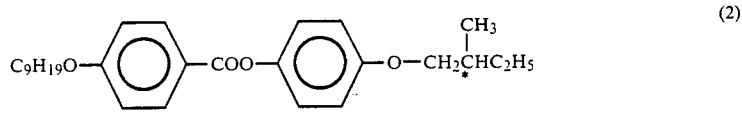
(2)

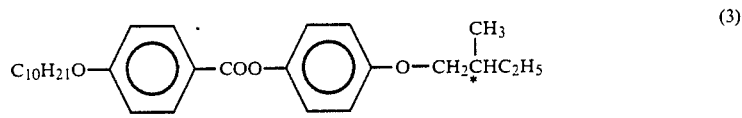
(3)

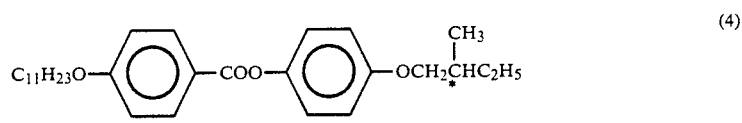
(4)

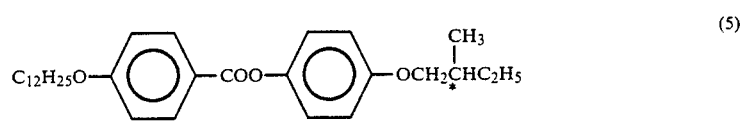
(5)

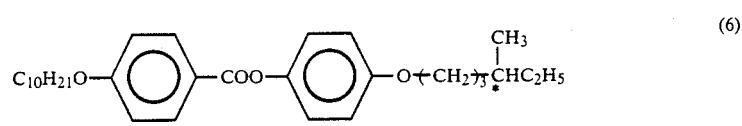
(6)

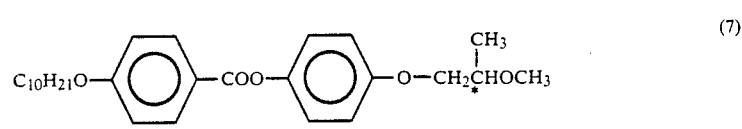
(7)

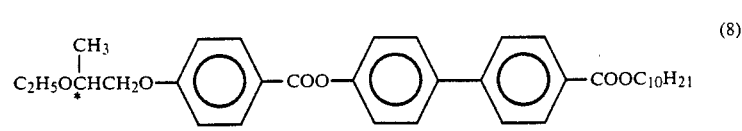
(8)

-continued
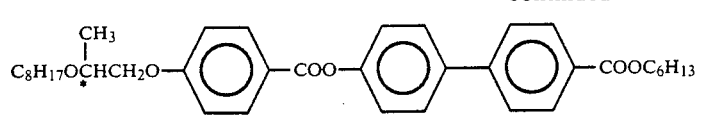  (9)
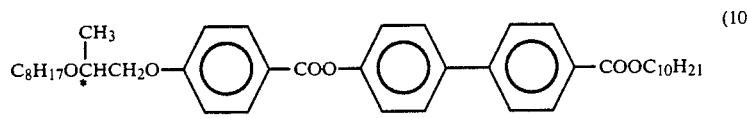  (10)
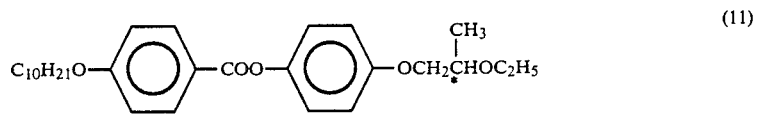  (11)
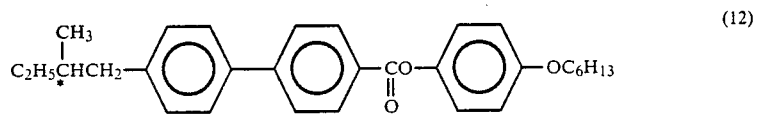  (12)
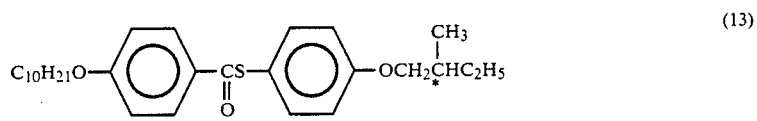  (13)
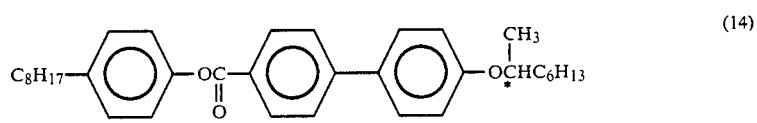  (14)
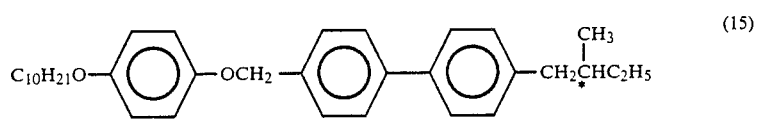  (15)
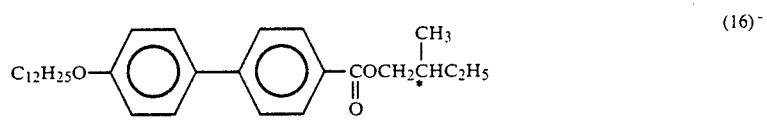  (16)
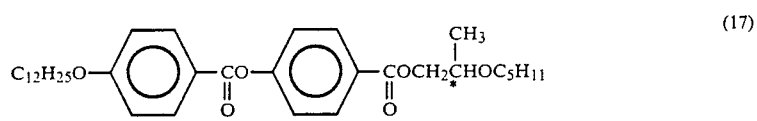  (17)
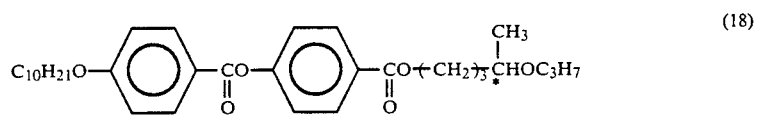  (18)
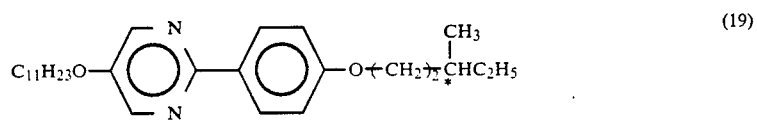  (19)
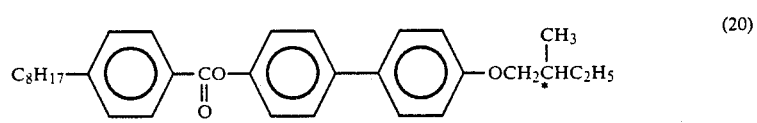  (20)
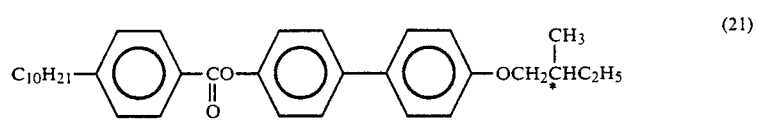  (21)

-continued
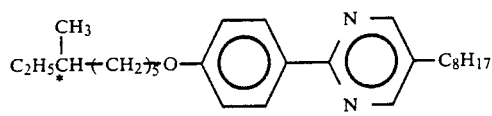 (22)
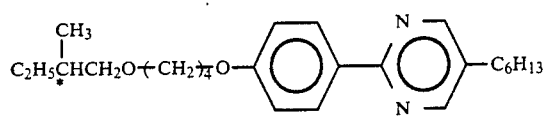 (23)
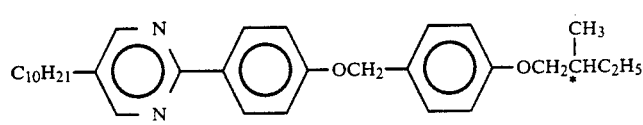 (24)
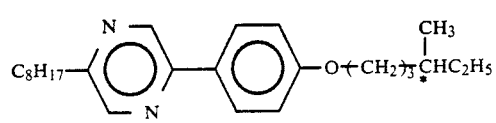 (25)
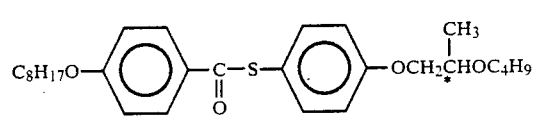 (26)
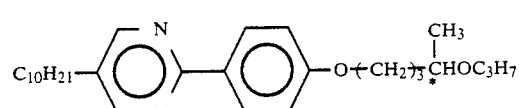 (27)
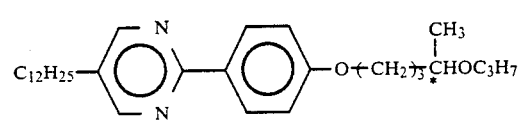 (28)
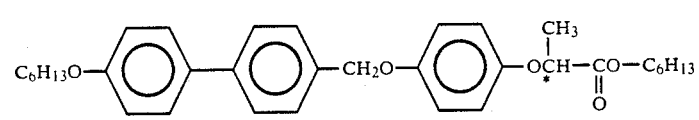 (29)
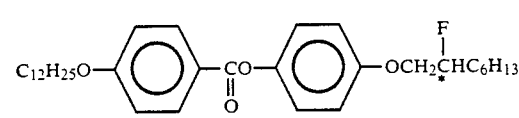 (30)
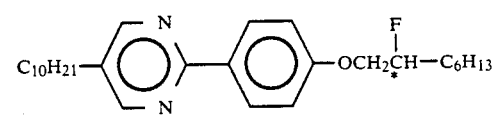 (31)
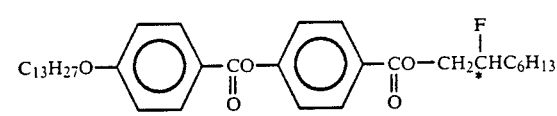 (32)
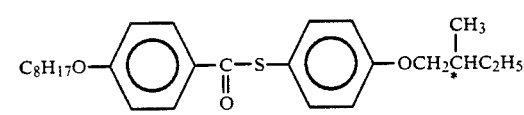 (33)
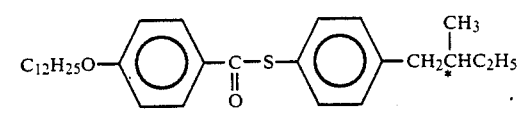 (34)

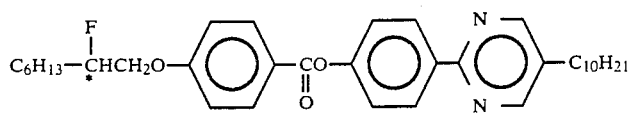
(35)
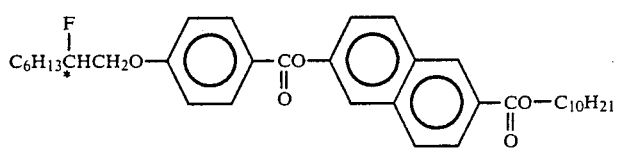
(36)
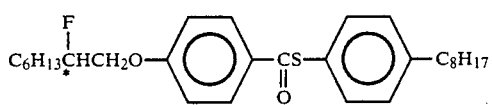
(37)
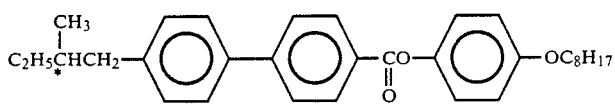
(38)
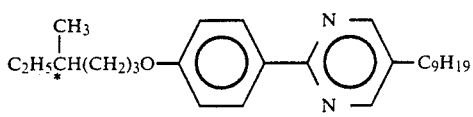
(39)
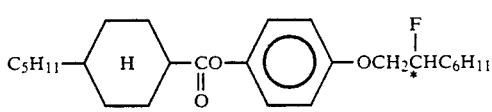
(40)
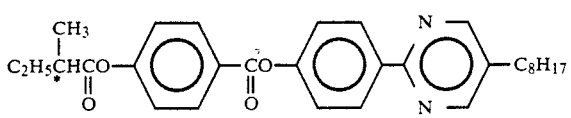
(41)
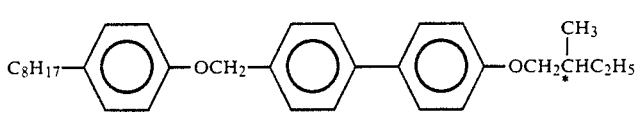
(42)
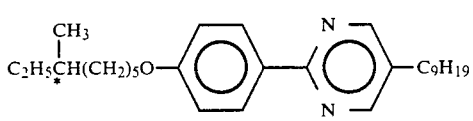
(43)
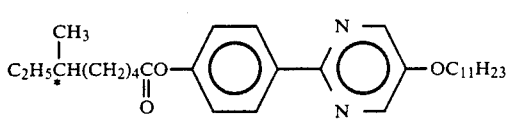
(44)
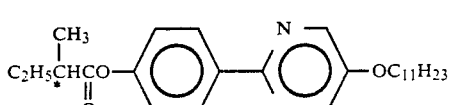
(45)
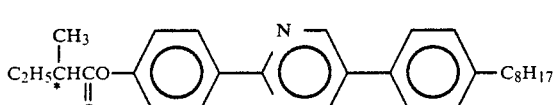
(46)
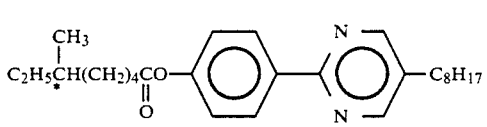
(47)

-continued
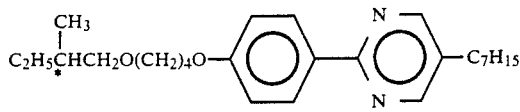 (48)
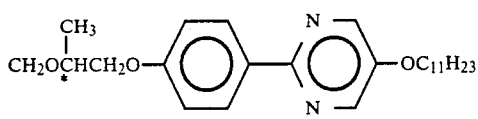 (49)
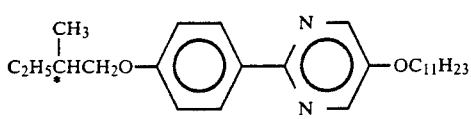 (50)
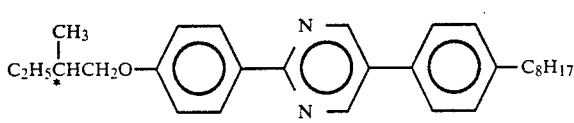 (51)
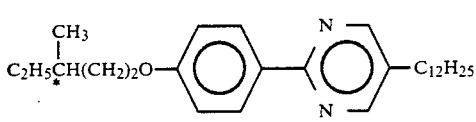 (52)
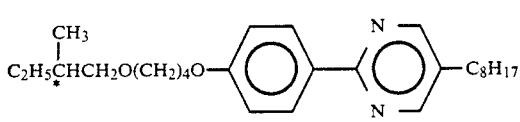 (53)
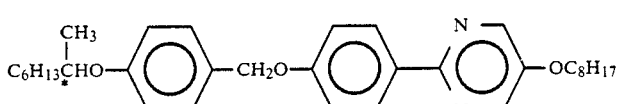 (54)
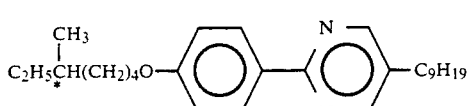 (55)
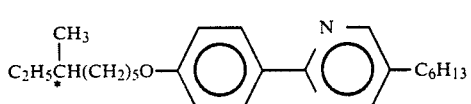 (56)
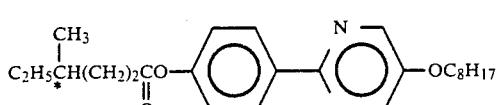 (57)
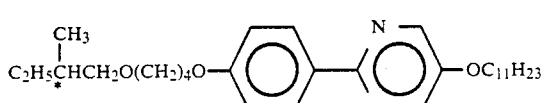 (58)
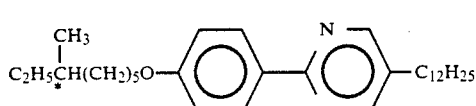 (59)
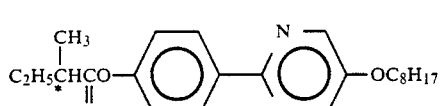 (60)

-continued
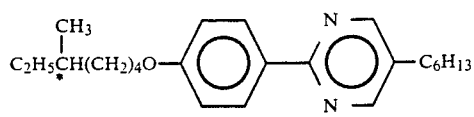 (61)
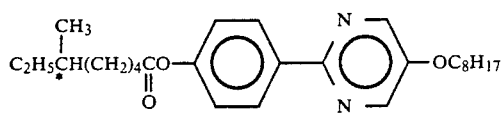 (62)
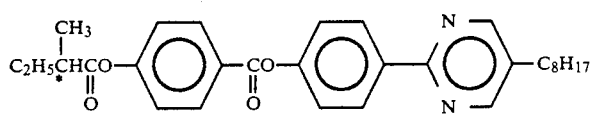 (63)
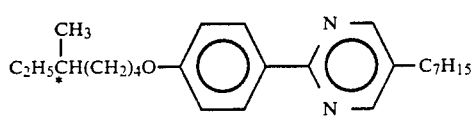 (64)
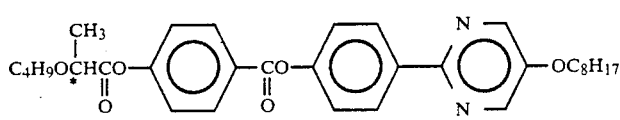 (65)
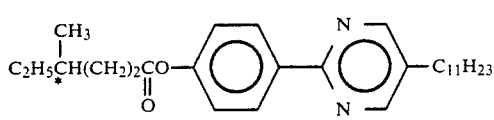 (66)
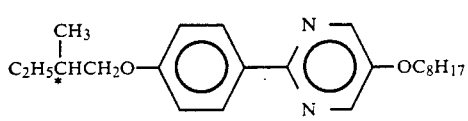 (67)
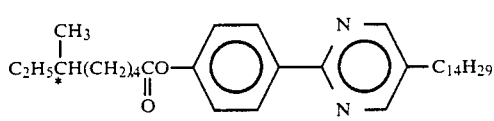 (69)
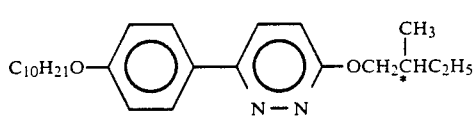 (70)
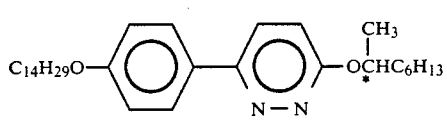 (71)
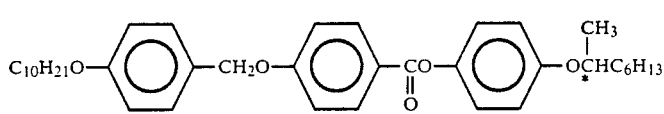 (72)
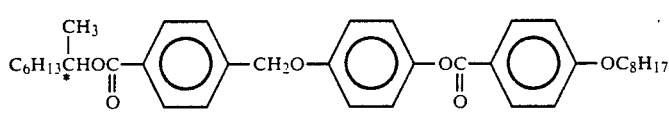 (73)
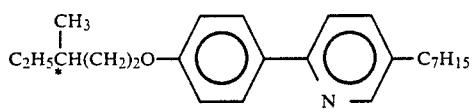 (74)

-continued
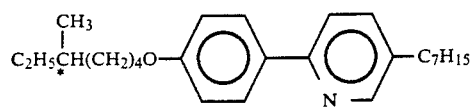 (75)
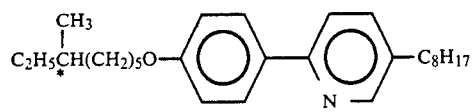 (76)
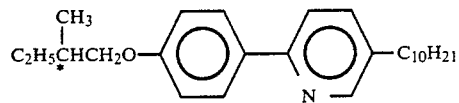 (77)
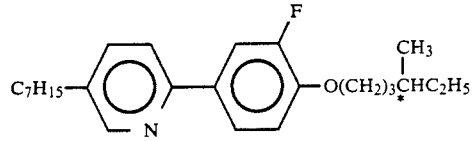 (78)
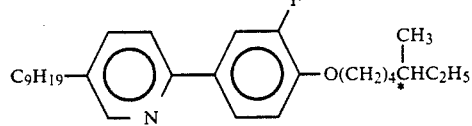 (79)
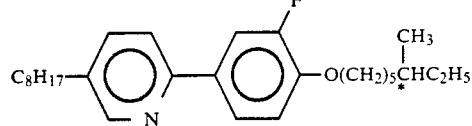 (80)
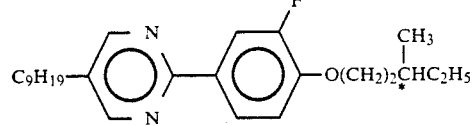 (81)
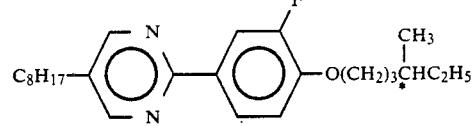 (82)
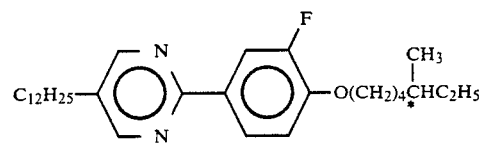 (83)
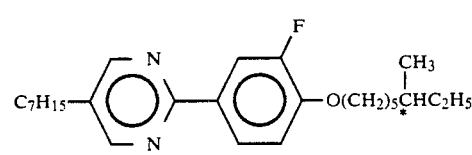 (84)
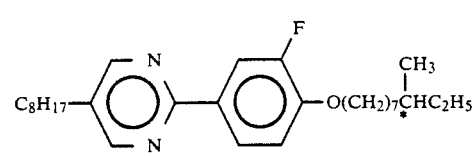 (85)

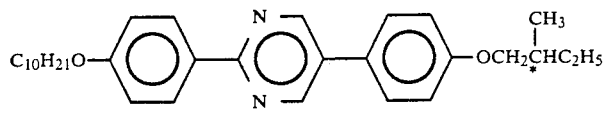 (86)
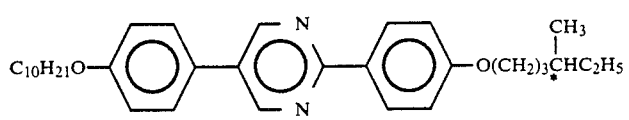 (87)
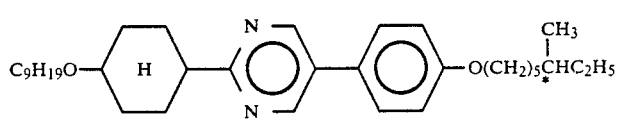 (88)
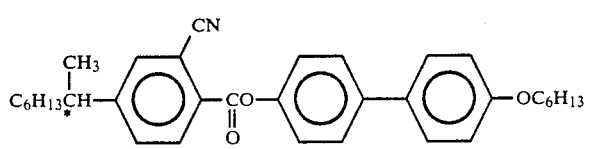 (89)
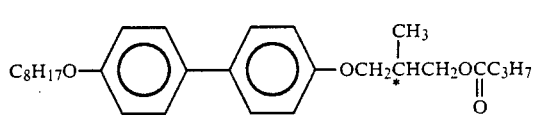 (90)
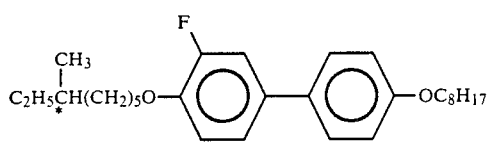 (91)
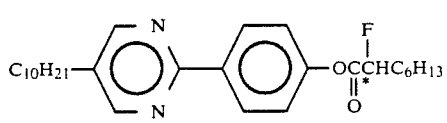 (92)
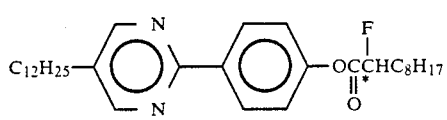 (93)
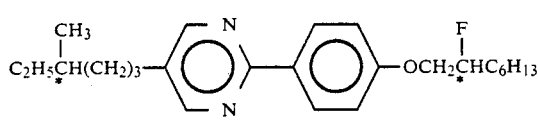 (94)
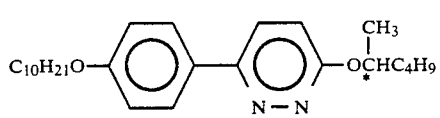 (95)
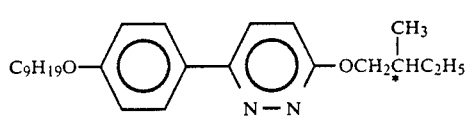 (96)
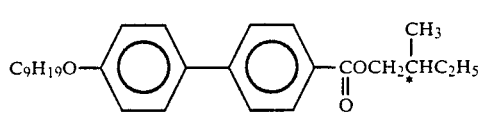 (97)
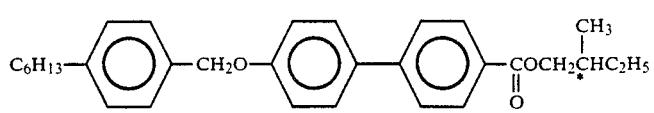 (98)

-continued
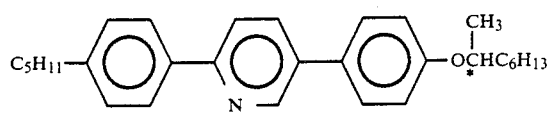
(99)
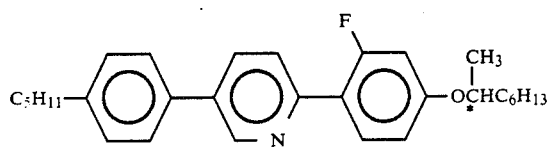
(100)
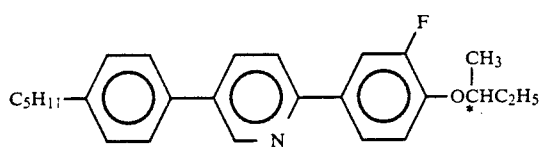
(101)
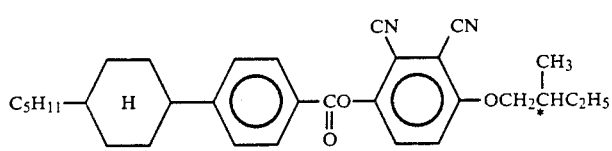
(102)
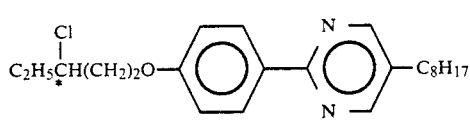
(103)
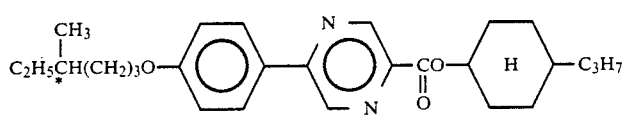
(104)
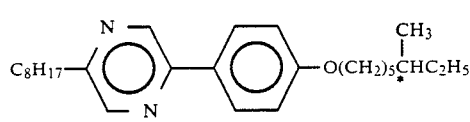
(105)
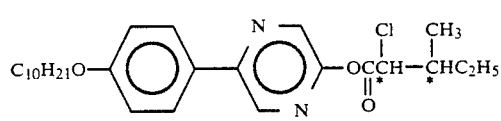
(106)
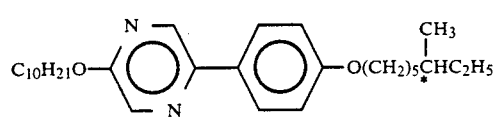
(107)
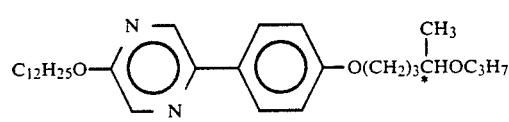
(108)
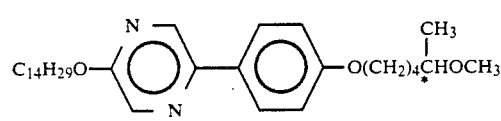
(109)
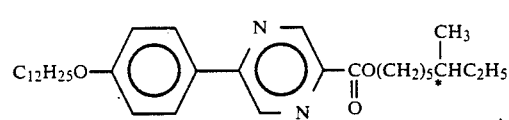
(110)

-continued
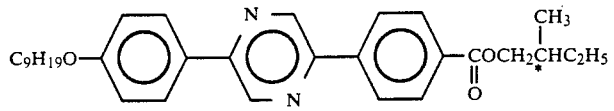 (111)
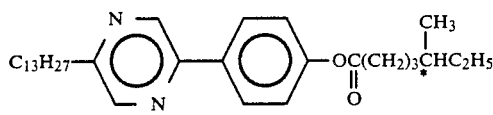 (112)
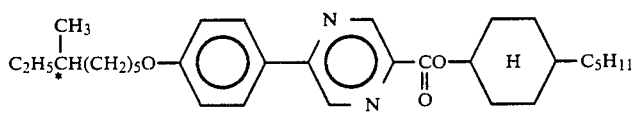 (113)
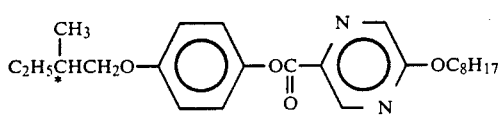 (114)
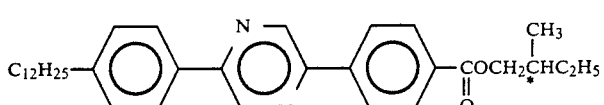 (115)
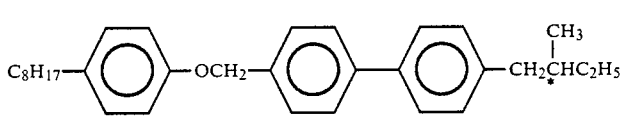 (116)
Class B: Mesomorphic compounds having non-chiral smectic phase and (or) nematic phase.
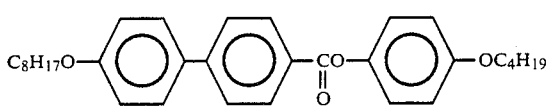 CRC/1/
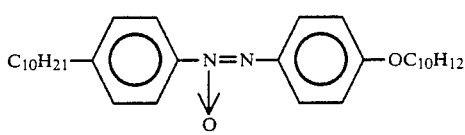 CRC/2/
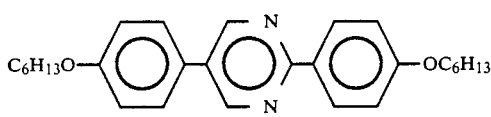 CRC/3/
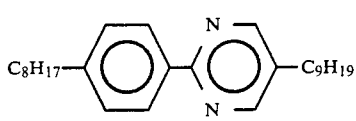 CRC/4/
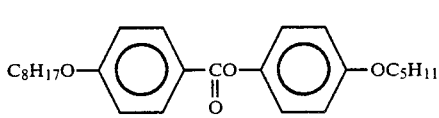 CRC/5/
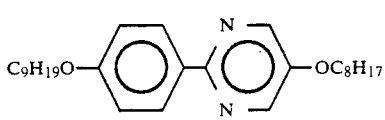 CRC/6/

-continued
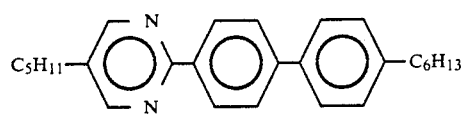 CRC/7/
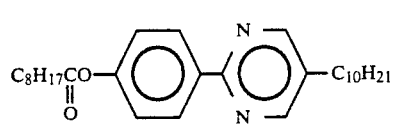 CRC/8/
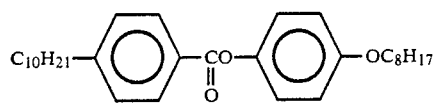 CRC/9/
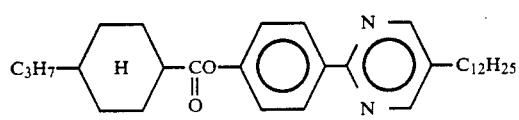 10
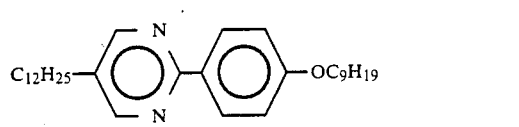 11
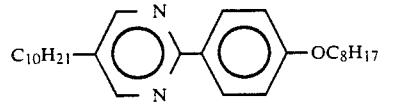 12
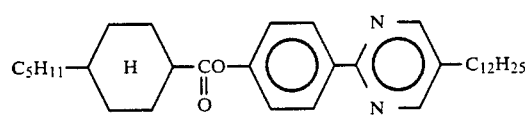 13
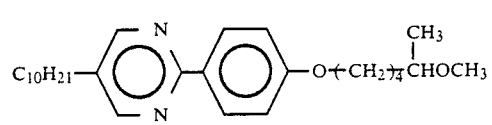 14
(racemate)
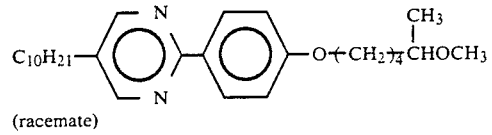 15
(racemate)
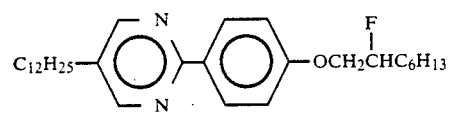 17
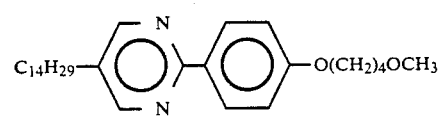 18
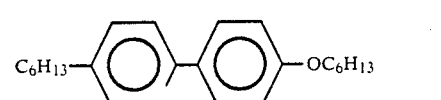 19
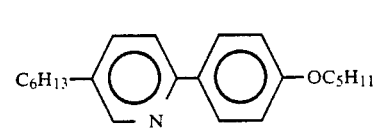 20
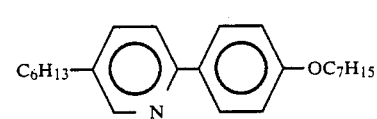

-continued
21
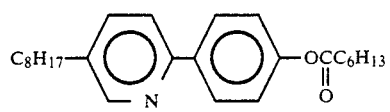
22
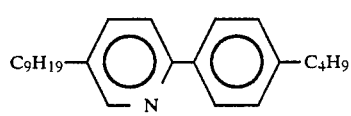
23
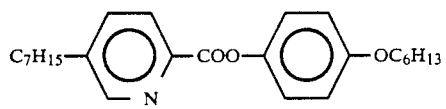
24
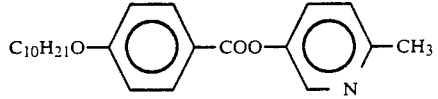
25
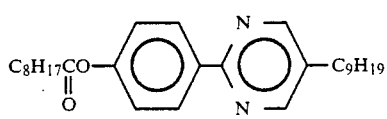
26
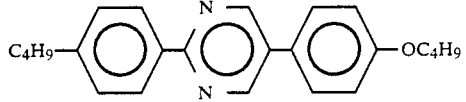
27
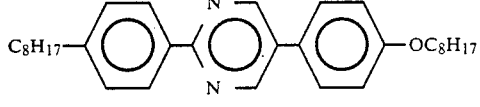
28
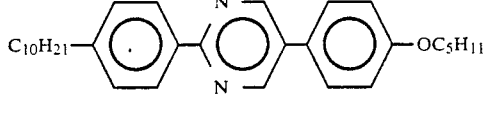
29
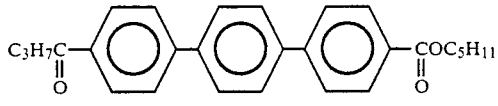
30
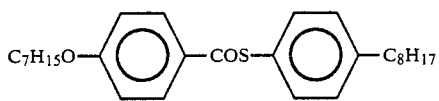
31
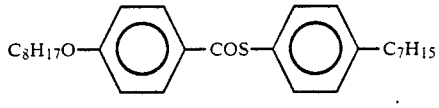
32
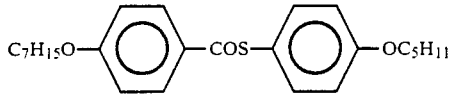
33
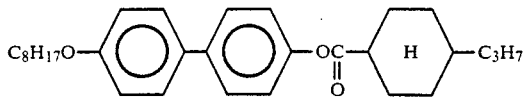

-continued
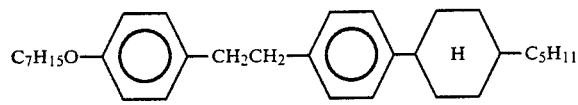 34
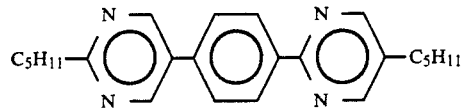 35
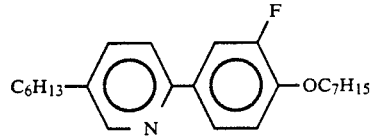 36
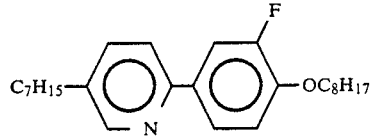 37
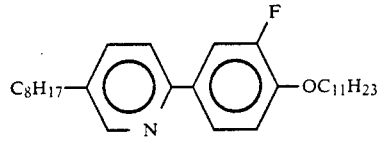 39
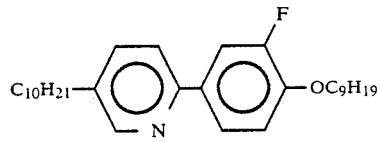 40
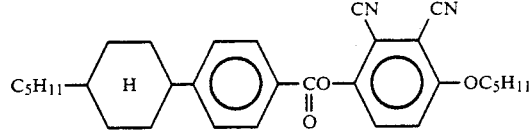 41
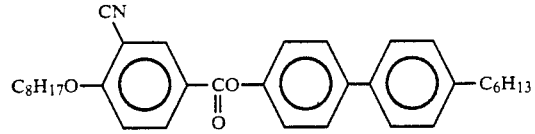 42
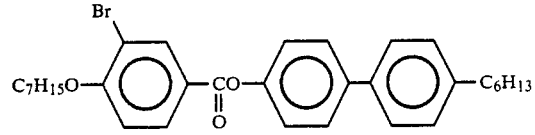 43
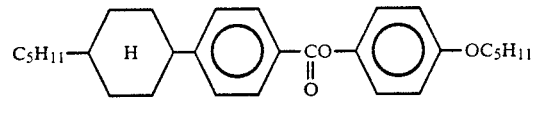 44
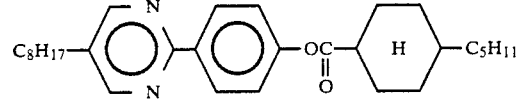 45
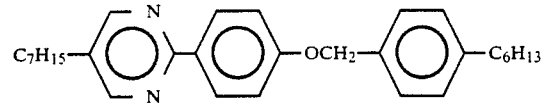 46

-continued
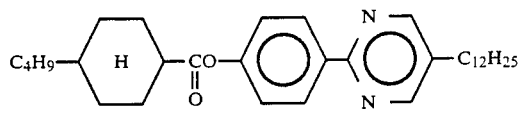 47
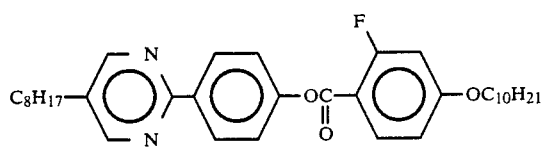 48
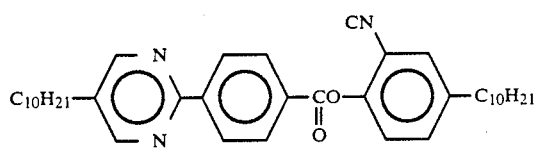 49
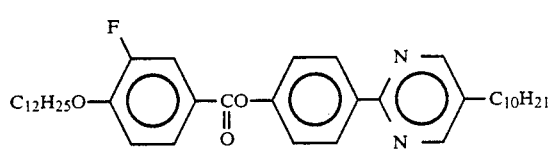 50
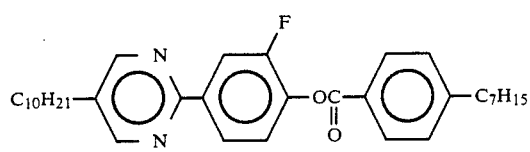 51
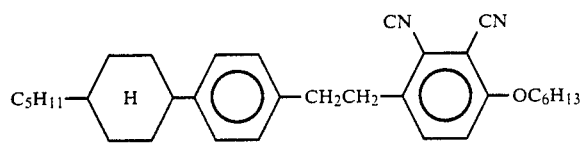 52
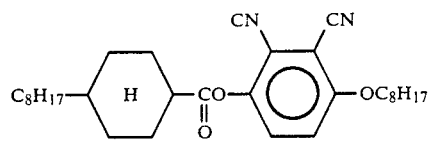 53
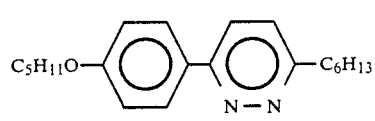 54
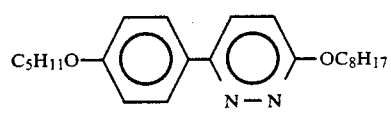 55
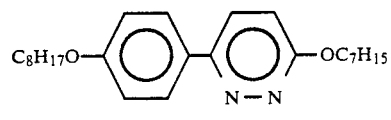 56
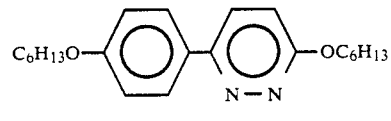 57
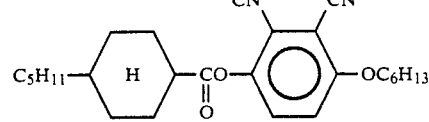 58

-continued
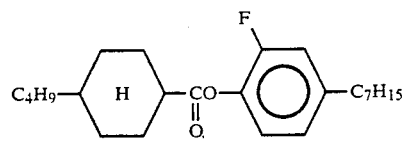
59
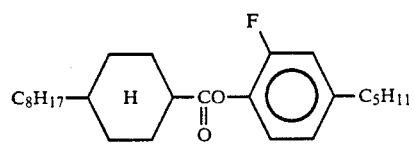
60
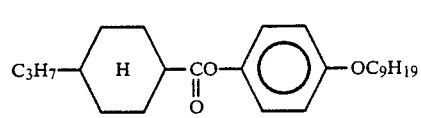
61
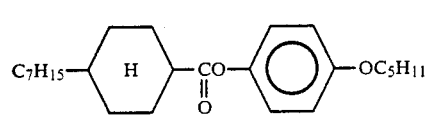
62
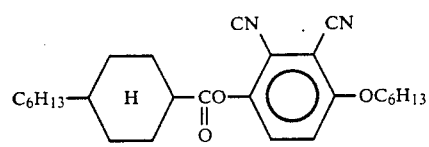
63
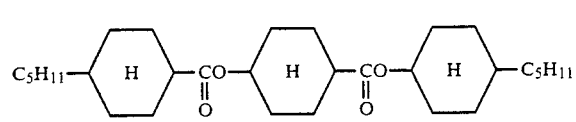
64
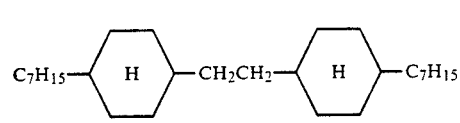
65
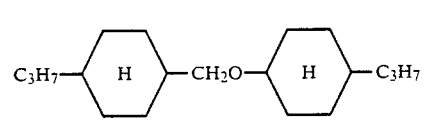
66
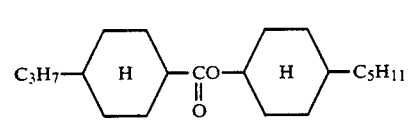
67
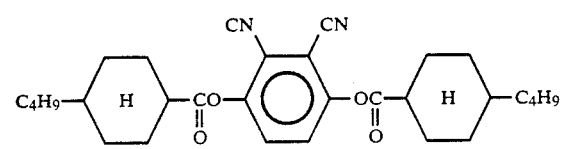
68
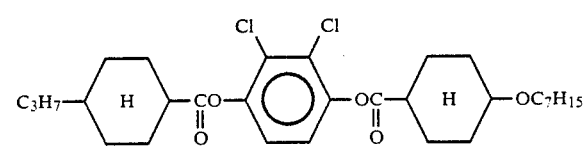
69
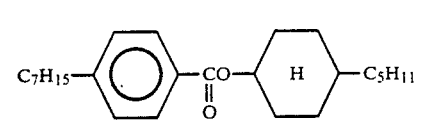
70

-continued
71
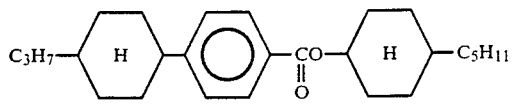
72
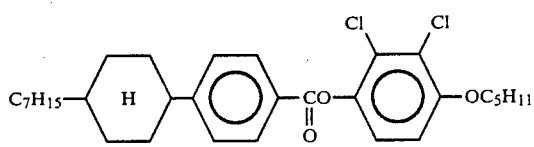
73
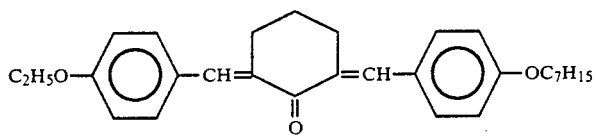
74
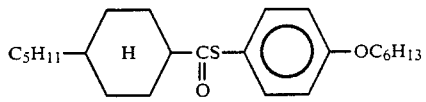
75
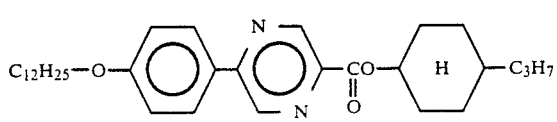
76
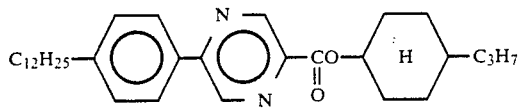
77
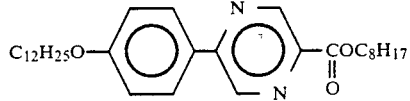
78
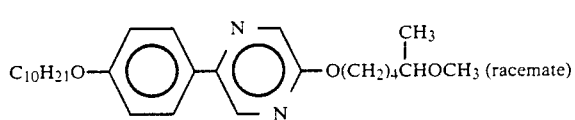
79
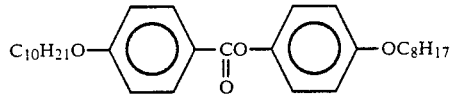
80
81
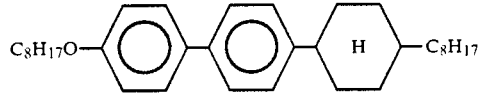
83
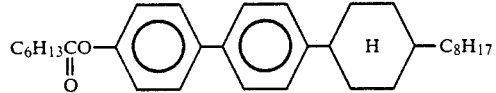
84
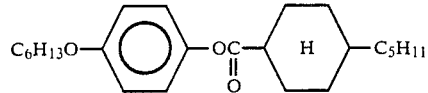

Hereinbelow the present invention will be explained in further detail based on Examples which should however be not construed to restrict the scope of the present invention.

In the following examples, the values of Δε (dielectric anisotropy) were obtained in the following measurement.

A 5 micron-thick homogeneous alignment cell having an electrode of 0.7 m² in area and a homogeneous alignment layer (rubbed polyimide) on both substrates, and a 5 micron-thick homeotropic alignment cell having an electrode of 0.7 cm² in area and a homeotropic alignment layer (aligning agent: "ODS-E" available from Chisso K.K.) on both substrates, were provided. The respective cells were filled with a sample liquid crystal material (compound or composition) to prepare liquid crystal devices. The capacitances of the liquid crystal layers were measured by applying a sine wave with a frequency of 100 kHz and amplitudes of ±0.5 V to the respective devices at a prescribed temperature set for the liquid crystal material, and the dielectric constants $\epsilon \parallel$ and $\epsilon \perp$ were obtained from the measured capacitance values of the respective devices, whereby the dielectric anisotropy Δε was calculated by the equation of $\Delta\epsilon = \epsilon\parallel - \epsilon\perp$.

EXAMPLE 1

Synthesis of 2-n-decyl-5-[4-(trans-4'-n-pentylcyclohexylcarbonyloxy)phenyl]-1,3,4-oxadiazole (Example compound A-3).

Into a mixture solution of 1.5 g (4.97×10⁻³ mol) of 2-n-decyl-5-[4-hydroxyphenyl]-1,3,4-oxadiazole, 2.5 ml of dry pyridine and 2.5 ml of dry toluene, a solution of 1.08 g (4.97×10⁻³ mol) of trans-4-n-pentylcyclohexanecarbonyl chloride in 2.5 ml of dry toluene was added dropwise below 5° C. in 20 minutes, followed by stirring for 27 hours at room temperature. After the reaction, the reaction liquid was poured into 50 ml of iced water and acidified to pH 1 with 6N-HCl, followed by extraction with benzene, washing with water, dehydration and distilling-off of the solvent (benzene) to obtain a crude product. The crude product was purified by silica gel column chromatography with the use of an n-hexane/ethyl acetate=5/1 mixture solvent and recrystallized from ethanol to obtain 1.92 g of 2-n-decyl-5-[4-(trans-4'-n-pentylcyclohexylcarbonyloxy)-phenyl]-1,3,4-oxadiazole. (Yield: 80.1 %)

Phase Transition

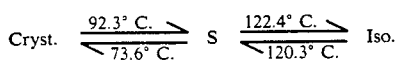

Cryst.: crystal
S: smectic
Iso.: isotropic phase
Δε: −2.8 (at 110° C., 100 kHz)

EXAMPLES 2, 3 and 4

Three dielectric mesomorphic compounds represented by the formula [I] were synthesized in the same manner as in Example 1 except that the 2-n-decyl-5-[4-hydroxyphenyl]-1,3,4-oxadiazole used in Example 1 was reacted with different acid chlorides as follows.

EXAMPLE 2

Acid chloride: trans-4-n-propylcyclohexanecarbonyl chloride.
Product: 2-n-decyl-5-[4-(trans-4'-n-propylcyclohexylcarbonyloxy)-phenyl]-1,3,4-oxadiazole (Example compound A-2).

Phase Transition

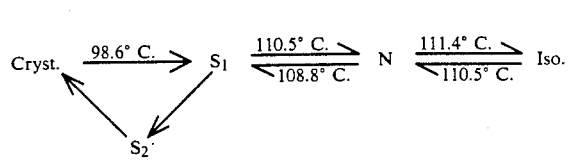

S₁, S₂ smectic phase (un-identified)
N: nematic phase.

EXAMPLE 3

Acid chloride: p-n-decylbenzoic acid chloride.
Product: 2-n-decyl-5-[4-(4'-n-decylbenzoyloxy)-phenyl]-1,3,4-oxadiazole. (Example compound A-12).

Phase Transition

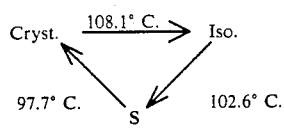

EXAMPLE 4

Acid chloride: 3-fluoro-4-n-octyloxybenzoic acid chloride.
Product: 2-n-decyl-5-[4-(3-fluoro-4'-n-octyloxybenzoyloxy)-phenyl]-1,3,4-oxadiazole (Example compound A-15).

Phase Transition

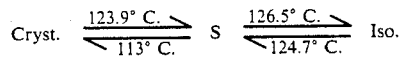

EXAMPLE 5

2-n-octyl-5-[4-hydroxyphenyl]-1,3,4-oxadiazole and trans-4-n-propylcyclohexanecarbonyl chloride were reacted in a similar manner as in Example 1 to obtain 2-n-octyl-5-[4-(trans-4'-n-propylcyclohexylcarbonyloxy)-phenyl]-1,3,4-oxadiazole. (Yield: 85 %)

Phase Transition

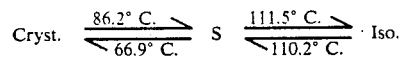

EXAMPLE 6

Synthesis of 2-n-decyl-5-[4-(trans-4'-n-propylcyclohexylmethyleneoxy)-phenyl]-1,3,4-oxadiazole (Example compound No. A-22).

1.5 g (4.97×10⁻³ mol) of 2-n-decyl-5-[4- hydroxyphenyl]-1,3,4-oxadiazole was dissolved in 20 ml of dimethylformamide, followed by addition of 0.75 g of 85% potassium hydroxide and 1 hour of stirring at 100° C. To the reaction mixture was added 1.54 g 4.97×10$^{-3}$ mol) of trans-4-n-propylcyclohexylmethyl-p-toluenesulfonate, and the mixture was further stirred for 4 hours at 100° C. After the reaction, the reaction mixture was poured into 200 ml of iced water, followed by extraction with benzene, washing with water, dehydration and distilling off of the solvent to obtain a crude product, which was purified by silica gel column chromatography and recrystallized from ethanol to obtain 0.94 g of 2-n-decyl-5-[4-(trans-4'-n-propylcyclohexyl-methyleneoxy)-phenyl]-1,3,4-oxadiazole. (Yield: 43.2 %).

Phase Transition $$\text{Cryst.} \underset{42.6° C.}{\overset{72.1° C.}{\rightleftarrows}} S \underset{98.4° C.}{\overset{100.4° C.}{\rightleftarrows}} \text{Iso.}$$

EXAMPLE 7

A liquid crystal composition A was prepared by mixing a ferroelectric mesomorphic compound example (9) selected from the above-mentioned Class A and a mesomorphic compound example A-2 represented by the formula (I) in a weight ratio of 4:1. The above ferroelectric mesomorphic compound (9) and the liquid crystal composition A were respectively sandwiched between a pair of electrode plates each having a rubbing-treated polyimide coating film and disposed with a gap of 2 microns from each other to prepare two liquid crystal devices. These liquid crystal devices were respectively subjected to measurement of a response time by detecting an optical response under right angle cross nicols when subjected application of an electric field with a peak-to-peak voltage of 20 V. The results are shown below:

|  | 40° C. | 25° C. |
|---|---|---|
| Ferroelectric mesomorphic compound (9) | 400 μs. | 610 μs. |
| Liquid crystal composition A | 280 μs. | 420 μs. |

The above results show that the addition of a mesomorphic compound according to the invention [Example A-2] to a ferroelectric mesomorphic compound [Example (9)] provided an improved responsiveness.

EXAMPLE 8

A liquid crystal composition B was prepared by mixing ferroelectric mesomorphic compound examples (1) and (38) selected from the class A in a ratio of 4:1.

Then, the liquid crystal composition B and a mesomorphic compound example A-23 represented by the formula (I) were mixed in a ratio of 9:1 to prepare a liquid crystal composition C.

The liquid crystal compositions B and C were used in the same manner as in Example 7 to prepare liquid crystal devices, which were then subjected to measurement of a response time in the same manner as in Example 7 except that the application voltage was changed to 30 V. The results are shown below.

|  | 35° C. | 25° C. |
|---|---|---|
| Liquid crystal composition B | 685 μs. | 1275 μs. |
| Liquid crystal composition C | 450 μs. | 680 μs. |

The above results show that the addition of the mesomorphic compound example A-23 according to the invention to the liquid crystal composition B provided an improved responsiveness.

EXAMPLE 9

A liquid crystal composition D was prepared by mixing the liquid crystal composition B used in Example 7, a non-chiral smectic mesomorphic compound example CRC/10/ selected from the class B, and mesomorphic compound examples A-3 and A-12 represented by the formula (I) in ratios of B: CRC/10/ :A-3:A-12 = 14:4:1:1.

A liquid crystal device was prepared by using the above liquid crystal composition D otherwise in quite the same manner as in Example 7 and subjected to measurement of a response time under the same conditions as in Example 7. The results are shown below together with those obtained by using the liquid crystal composition B.

|  | 35° C. | 25° C. |
|---|---|---|
| Liquid crystal composition B (Example 7) | 685 μs. | 1275 μs. |
| Liquid crystal composition D | 470 μs. | 620 μs. |

The above results show that the combined addition of the mesomorphic compound examples A-3 and A-12 according to the invention and the non-chiral smectic mesomorphic compound CRC/10/ to the liquid crystal composition B provided a further improved responsiveness.

EXAMPLE 10

A commercially available ferroelectric liquid crystal ("CS-1014" available from Chisso K.K.) having a Δε of nearly 0 (Δε≠−0.4 (sin wave, 100 kHz)) and a mesomorphic compound example A-22 represented by the formula (I) of the invention were mixed in a ratio of 92:8 to prepare a liquid crystal composition E.

Liquid crystal devices were prepared in the same manner as in Example 7 except that the above liquid crystal CS1014 and the liquid crystal composition E were used respectively and the liquid crystal layer thicknesses were changed to 1.5 microns.

The above liquid crystal devices were subjected to measurement of a tilt angle under right angle cross nicols at 25° C. to provide 7 degrees for CS1014 and 7.2 degrees for the liquid crystal composition E. Then, the devices were subjected to application of a ±8 V rectangular waveform at a frequency of 60 kHz, and the tilt angles were measured under the voltage application and microscopic observation to provide 8.8 degrees for CS1014 and 11.4 degrees for the liquid crystal composition E. Under these conditions, the transmittances were measured to be 7.8% for CS1014 and 11 % for the composition E. Further, the contrast ratios were measured to be 8:1 for CS1014 and 30:1 for the composition E.

The above results show the addition of the mesomorphic compound example A-22 represented by the formula (I) of the present invention to a liquid crystal CS1014 having a of nearly 0 provided a liquid crystal device showing improved display characteristics.

EXAMPLE 11

Synthesis of 2-n-decyl-5-[4-(trans-4'-n-propylcyclohexylcarbonyloxy)phenyl]-1,3,4-thiadiazole (Example compound B-20).

Into a mixture solution of 1.2 g ($3.77 \times 10^{-3}$ mol) of 2-n-decyl-5-[4-hydroxyphenyl]-1,3,4-thiadiazole, 2.5 ml of dry pyridine and 2.5 ml of dry toluene, a solution of 0.71 g ($3.77 \times 10^{-3}$ mol) of trans-4-n-propylcyclohexanecarbonyl chloride in 2.5 ml of dry toluene was added dropwise below 5° C. in 15 minutes, followed by stirring for 19 hours at room temperature. After the reaction, the reaction liquid was poured into 50 ml of iced water and acidified to pH 1 with 6N-HCl, followed by extraction with benzene, washing with water dehydration and distilling-off of the solvent (benzene) to obtain a crude product. The crude product was purified by silica gel column chromatography with the use of an n-hexane/ethyl acetate=3/1 mixture solvent and recrystallized from ethanol to obtain 1.15 g of 2-n-decyl-5-[4-(trans-4'-n-propylcyclohexylcarbonyloxy)-phenyl]-1,3,4-thiadiazole. (Yield: 64.9%)

Phase transition (numeral denotes temperature in °C.)

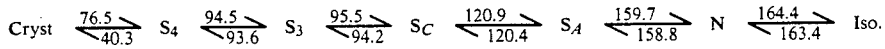

$S_1$-$S_4$: smectic phase (un-identified)
$S_A$: smectic A phase, $S_C$: smectic C phase.
IR (cm$^{-1}$)
2925, 2850, 1740, 1600, 1510, 1470, 1450, 1205, 1165, 1130, 980, 862
$\Delta\epsilon$: $-3.3$ (at 100° C., 100 kHz).

EXAMPLE 12

2-n-decyl-5-[4-(trans-4'-n-pentylcyclohexylcarbonyloxy)-phenyl]-1,3,4-thiadiazole (Example compound B-34) was prepared in the same manner as in Example 11 except that trans-4-n-pentylcyclohexanecarbonyl chloride was used instead of trans-4-n-propylcyclohexanecarbonyl chloride. Yield: 60.2 % .

Phase Transition

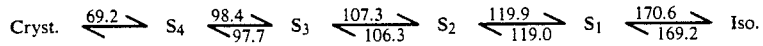

IR (cm$^{-1}$)
2860, 2825, 1750, 1600, 1508, 1470, 1450, 1205, 1162, 1135, 980, 860

EXAMPLE 13

Synthesis of 2-n-decyl-5-[4-(trans-4'-n-propylcyclohexylmethyleneoxy)-phenyl]-1,3,4-thiadiazole (Example compound N. B-3).

1.0 g ($3.28 \times 10^{-3}$ mol) of 2-n-decyl-5-[4-hydroxyphenyl]-1,3,4-thiadiazole was dissolved in 20 ml of dimethylformamide, followed by addition of 0.5 g of 85 % potassium hydroxide and 1 hour of stirring at 100° C. To the reaction mixture was added 1.02 g ($3.28 \times 10^{-3}$ mol) of trans-4-n-propylcyclohexylmethyl-p-toluenesulfonate, and the mixture was further stirred for 4 hours at 100° C. After the reaction, the reaction mixture was poured into 200 ml of iced water, followed by extraction with benzene, washing with water, dehydration and distilling off of the solvent to obtain a crude product, which was purified by silica gel column chromatography and recrystallized from ethanol to obtain 0.8 g of 2-n-decyl-5-[4-(trans-4'-n-propylcyclohexylmethyleneoxy)-phenyl]-1,3,4-thiadiazole. (Yield: 53.3 %).

Phase Transition

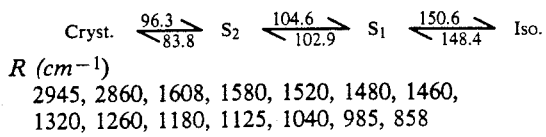

R (cm$^{-1}$)
2945, 2860, 1608, 1580, 1520, 1480, 1460, 1320, 1260, 1180, 1125, 1040, 985, 858

EXAMPLE 14

Synthesis of 2-(1-methylpropyl)-5-[4-(trans-4-n-pentylcyclohexylcarbonyloxy)phenyl]-1,3,4-thiadiazole (Example compound B-51).

Into a mixture of 0.3 g ($1.28 \times 10^{-3}$ mol) of 1-methylpropyl-5-[4-hydroxyphenyl]-1,3,4-thiadiazole, 0.26 g ($1.31 \times 10^{-3}$ mol) of trans-4-n-pentylcyclohexanecarboxylic acid, 0.27 g ($1.31 \times 10^{-3}$ mol) of dicyclohexylcarbodiimide and 0.03 g of 4-(1-pyrrolidinyl)pyrimidine, 15 ml of methylene chloride was added, followed by 20 hours of stirring at room temperature. After the reaction, the reaction was filtered and the solid was washed with methylene chloride. The filtrate and the washing liquid were dehydrated, and the solvent was distilled off therefrom to obtain a crude product, which was then recrystallized twice to obtain 0.24 g of 2-(1-methylpropyl)-5-[4-(trans-4-n-pentylcyclohexylcarbonyloxy)-phenyl]-1,3,4-thiadiazole. (Yield: 45.2%).

Phase Transition

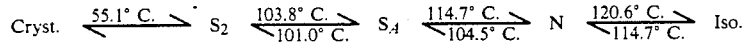

EXAMPLE 15

A liquid crystal composition F was prepared by mixing a ferroelectric mesomorphic compound example (9) selected from the above-mentioned Class A and a mesomorphic compound example B-7 represented by the formula (I) in a ratio of 4:1. The above ferroelectric mesomorphic compound (9) and the liquid crystal composition F were respectively sandwiched between a pair of electrode plates each having a rubbing-treated polyimide coating film and disposed with a gap of 2 microns from each other to prepare two liquid crystal devices in the same manner as in Example 7. These liquid crystal devices were respectively subjected to measurement of a response time by detecting an optical response under right angle cross nicols when subjected application of an electric field with a peak-to-peak voltage of 20 V. The results are shown below:

|                                    | 40° C.  | 25° C.  |
| ---------------------------------- | ------- | ------- |
| Ferroelectric mesomorphic compound (9) | 400 μs. | 610 μs. |
| Liquid crystal composition F       | 320 μs. | 435 μs. |

The above results show that the addition of a mesomorphic compound according to the invention [Example B-7] to a ferroelectric mesomorphic compound [Example (9)] provided an improved responsiveness.

EXAMPLE 16

A liquid crystal composition B was prepared by mixing ferroelectric mesomorphic compound examples (1) and (38) selected from the class A in a ratio of 4:1.

Then, the liquid crystal composition B and a mesomorphic compound example B-2 represented by the formula (I) were mixed in a ratio of 9:1 to prepare a liquid crystal composition G.

The liquid crystal compositions B and G were used in the same manner as in Example 15 to prepare liquid crystal devices, which were then subjected to measurement of a response time in the same manner as in Example 15 except that the application voltage was changed to 30 V. The results are shown below.

|                               | 35° C.   | 25° C.    |
| ----------------------------- | -------- | --------- |
| Liquid crystal composition B  | 685 μs.  | 1275 μs.  |
| Liquid crystal composition G  | 510 μs.  | 820 μs.   |

The above results show that the addition of the mesomorphic compound example B-2 according to the invention to the liquid crystal composition B provided an improved responsiveness.

EXAMPLE 17

A liquid crystal composition H was prepared by mixing the liquid crystal composition B used in Example 16, a non-chiral smectic mesomorphic compound example CRC/10/ selected from the class B, and mesomorphic compound examples B-3 and B-34 represented by the formula (I) in ratios of B: CRC/10/ :B-3:B-34 = 14:4:1:1.

A liquid crystal device was prepared by using the above liquid crystal composition H otherwise in quite the same manner as in Example 15 and subjected to measurement of a response time under the same conditions as in Example 15. The results are shown below together with those obtained by using the liquid crystal composition B.

|                                          | 35° C.   | 25° C.    |
| ---------------------------------------- | -------- | --------- |
| Liquid crystal composition B (Example 16) | 685 μs.  | 1275 μs.  |
| Liquid crystal composition D             | 520 μs.  | 670 μs.   |

The above results show that the combined addition of the mesomorphic compound examples B-3 and B-34 according to the invention and the non-chiral smectic mesomorphic compound CRC/10/ to the liquid crystal composition B provided a further improved responsiveness.

EXAMPLE 18

A commercially available ferroelectric liquid crystal ("CS-1014" available from Chisso K.K.) having a Δε of nearly 0 (Δε≃−0.4 (sine wave, 100 kHz)) and a mesomorphic compound example B-20 represented by the formula (I) of the invention were mixed in a ratio of 9:1 to prepare a liquid crystal composition I.

Liquid crystal devices were prepared in the same manner as in Example 15 except that the above liquid crystal CS1014 and the liquid crystal composition I were used respectively and the liquid crystal layer thicknesses were changed to 1.5 microns.

The above liquid crystal devices were subjected to measurement of a tilt angle under right angle cross nicols at 25° C. to provide 7 degrees for CS1014 and 8.2 degrees for the liquid crystal composition I. Then, the devices were subjected application of a ±8 V rectangular waveform at a frequency of 60 kHz, and the tilt angles were measured under the voltage application and microscopic observation to provide 8.8 degrees for CS1014 and 14.2 degrees for the liquid crystal composition I. Under these conditions, the transmittances were measured to be 7.8 % for CS1014 and 13 % for the composition E. Further, the contrast ratios were measured to be 8:1 for CS1014 and 40:1 for the composition E.

The above results show the addition of the mesomorphic compound example B-20 represented by the formula (I) of the present invention to a liquid crystal CS 1014 having a Δε of nearly 0 provided a liquid crystal device showing improved display characteristics.

EXAMPLE 19

A liquid crystal composition J was prepared by mixing optically active compound examples (8), (13), (17), (18), (20), (33), (34), (36) and (38) selected from the above-mentioned Class A, and non-chiral smectic or nematic mesomorphic compound examples CRC/1/ , CRC/5/ , CRC/6/ , CRC/7/ and CRC/9/ selected from the above-mentioned Class B in ratio of (8):(13):(17):(18):(20):(33):(34): (36):(38):CRC/1/ :CRC/5/ :CRC/6/ :E,crc/7/ :CRC/9/ :=10:9:10:10:5:6:3:5:5: 5:6:6:12:8.

Then, a liquid crystal composition K was prepared by mixing the above-prepared composition J and mesomorphic compound examples A-2, A-6, A-17, A-23, A-26, B-3, B-21 and B-33 represented by the formula (I) of the present invention in ratios of the composition J:A-2:A-6:A-17:A-23:A-26:B-3:B-21:B-33  80:3:2:3:3:2: 2:2:3.

The liquid crystal compositions J and K were used in the same manner as in Example 7 to prepare liquid crystal devices, which were then subjected to measurement of a response time in the same manner as in Example 7 except that the application voltage was changed to 30 V (peak-to-peak). The results are shown below.

|                               | 10° C.   | 25° C.   | 40° C.   |
| ----------------------------- | -------- | -------- | -------- |
| Liquid crystal composition J  | 980 μs.  | 358 μs.  | 135 μs.  |
| Liquid crystal composition K  | 900 μs.  | 362 μs.  | 137 μs.  |

Then, the above liquid crystal devices were subjected to measurement of tilt angles in the same manner as in Example 10 (under application of rectangular AC waveform of ±8 V and 60 kHz) to provide tilt angles of 8.3 degrees for the composition J and 13.8 degrees for the composition K.

The above results show that the addition of mesomorphic compounds according to the present invention to the liquid crystal composition J provided improvements in temperature-dependence of response speed as well as in display characteristics due to AC stabilization effect.

EXAMPLE 20

A liquid crystal composition L was prepared by mixing the composition J used in Example 19 and mesomorphic compound examples A-10, A-20, A-25, A-31, A-32, B-2, B-17, B-34, B-41 and B-43 represented by the formula (I) of the invention in ratios of the composition J:A-10:A-20:A-25:A-31:A-32:B-2:B-17:B-34: B-41:B-43 =80:2:2:2:1:1:3:2:5:1:1.

A liquid crystal device was prepared by using the above composition L otherwise in quite the same manner as in Example 19 and subjected to measurement of response time and tilt angle under the same conditions as in Example 19, whereby the following results were obtained.

| Response time | 10° C. | 25° C. | 40° C. |
|---|---|---|---|
| | 945 μs. | 370 μs. | 139 μs. |

Title angle: 14.3 degrees

The above results again show that the addition of mesomorphic compounds according to the present invention provides improvements in temperature-dependence of response speed and display characteristics due to AC stabilization effect.

As is understood from the results of the above examples, the liquid crystal composition and the liquid crystal device according to the present invention using the mesomorphic compound represented by the formula (I) show good responsiveness and remarkably improved display characteristic when applied to a display method utilizing the AC stabilization effect.

What is claimed is:

1. A ferroelectric liquid crystal composition comprising at least two mesomorphic compounds, at least one of which is represented by the following formula:

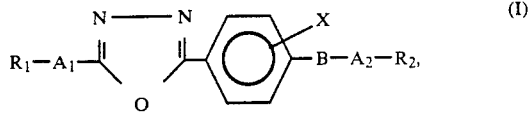

wherein $A_1$ denotes a single bond or

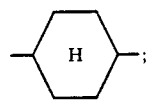

$A_2$ denotes

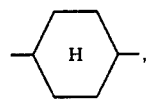

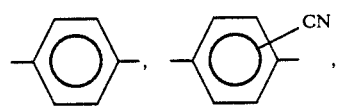

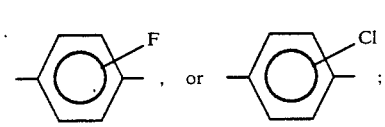

X denotes hydrogen, F or Cl; $R_1$ denotes a linear or branched alkyl group having 1-18 carbon atoms which may be substituted with Cl; $R_2$ denotes a linear or branched alkyl group, alkoxy group or alkoxycarbonyl group having 1-18 carbon atoms; and B denotes —O.-CO—, —CO.O—, —OCH$_2$ or —CH$_2$O—.

2. A composition according to claim 1, which contains 0.5-60 wt. % of the mesomorphic compound represented by the formula (I).

3. A composition according to claim 2, which contains 5-40 wt. % of the mesomorphic compound represented by the formula (I).

4. A composition according to claim 1, wherein the mesomorphic compound represented by the formula (I) is one of the following formulas A-1 to A-40:

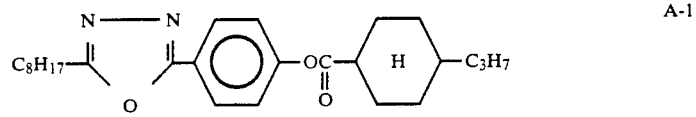

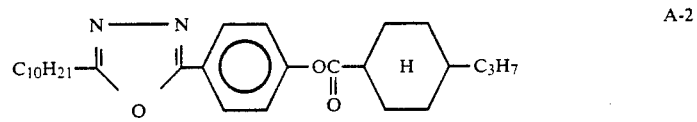

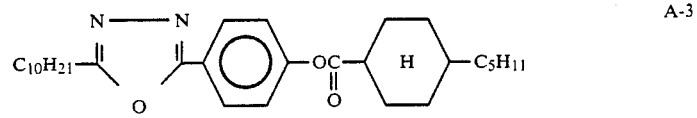

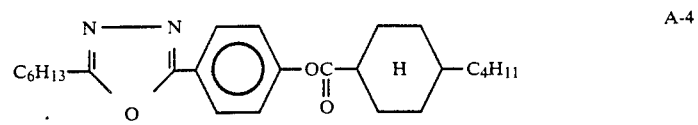

-continued
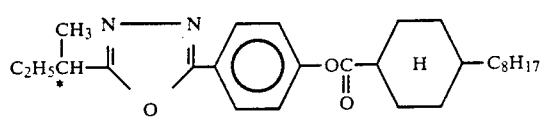 A-5
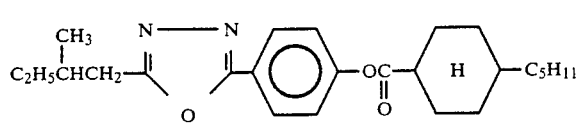 A-6
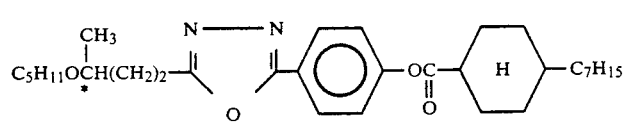 A-7
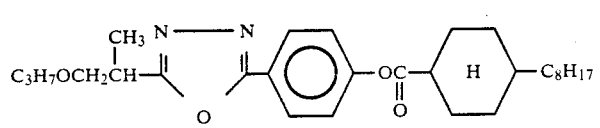 A-8
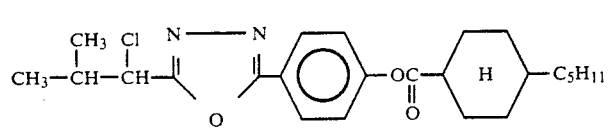 A-9
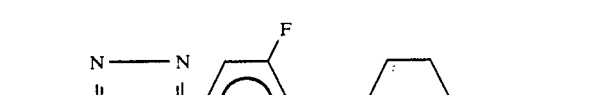 A-10
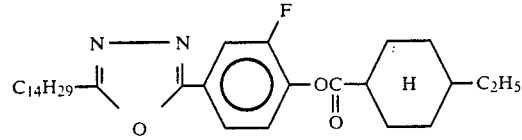 A-11
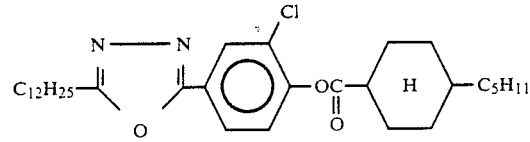 A-12
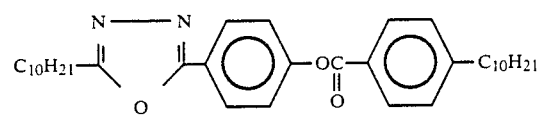 A-13
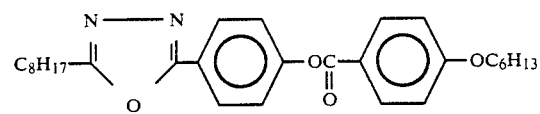 A-14
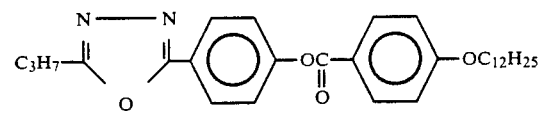 A-15
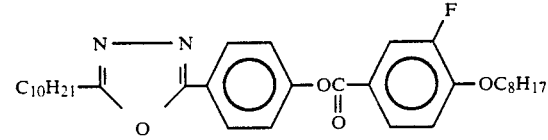 A-16
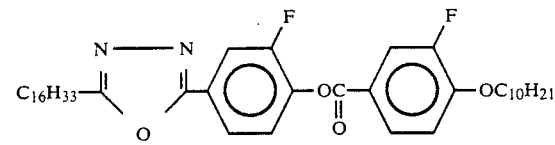

-continued
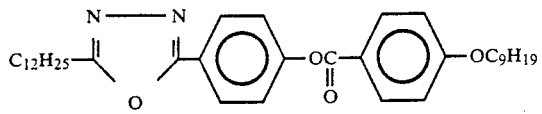 A-17
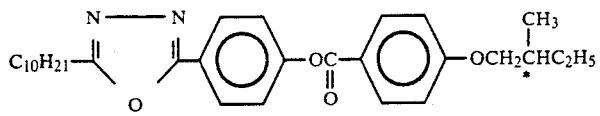 A-18
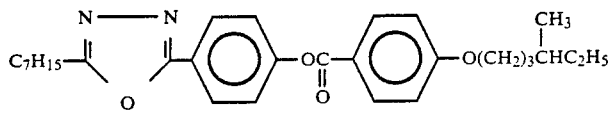 A-19
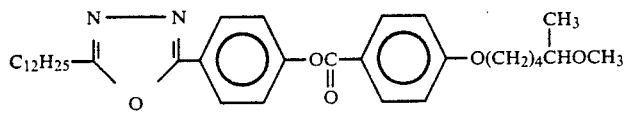 A-20
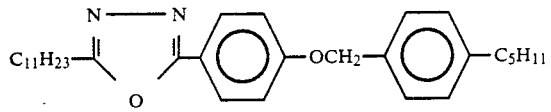 A-21
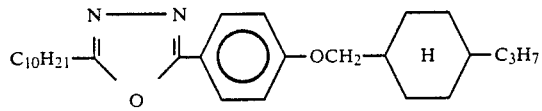 A-22
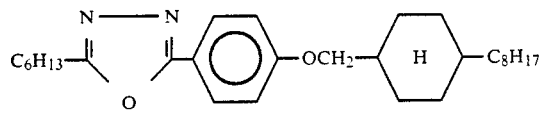 A-23
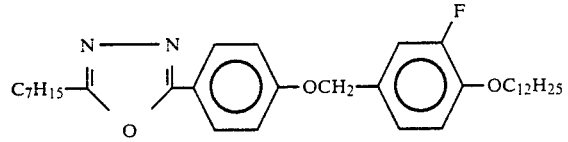 A-24
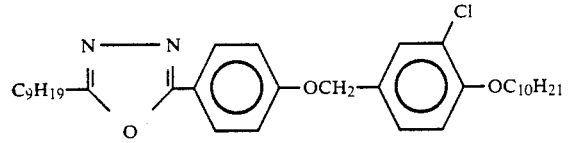 A-25
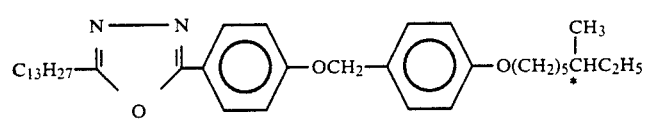 A-26
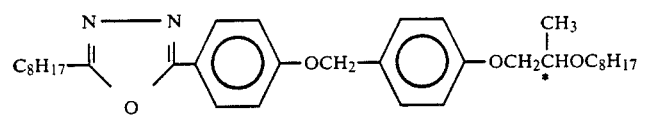 A-27
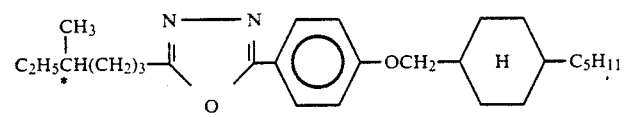 A-28
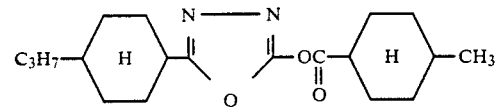 A-29

-continued
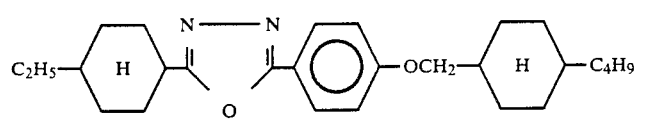 A-30
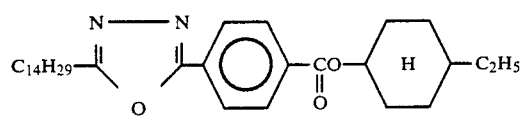 A-31
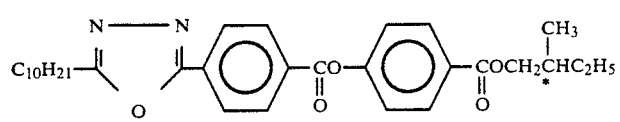 A-32
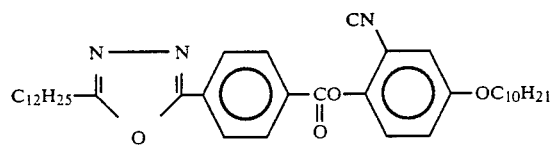 A-33
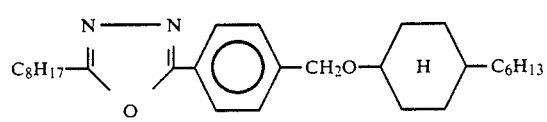 A-34
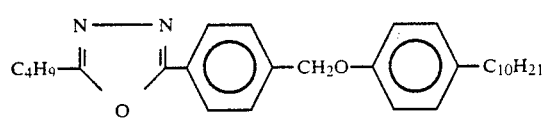 A-35
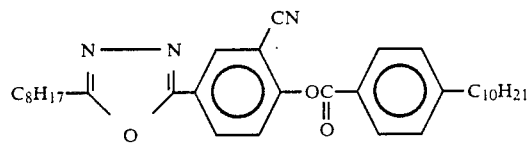 A-36
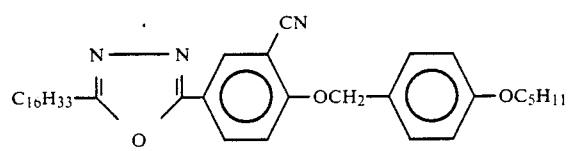 A-37
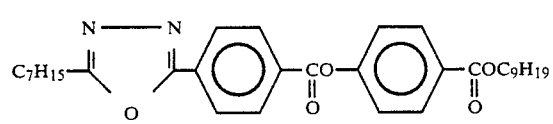 A-38
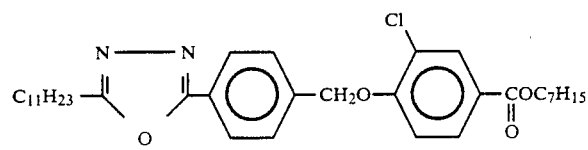 A-39
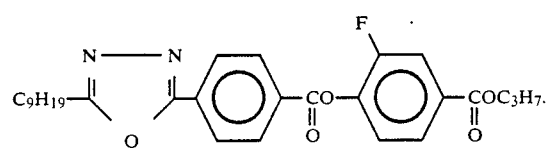 A-40
5. A ferroelectric liquid crystal device, comprising a pair of substrates and a ferroelectric liquid crystal composition disposed between said substrates, said ferroelectric liquid crystal composition comprising a mesomorphic compound represented by the following formula:

73

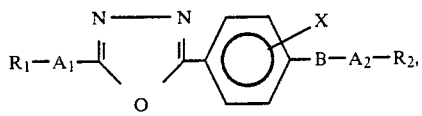

wherein A₁ denotes a single bond or

A₂ denotes

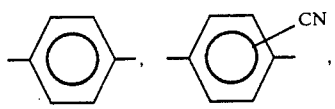

74

-continued

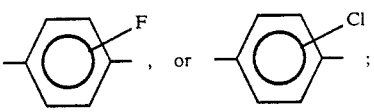

X denotes hydrogen, F or Cl; R₁ denotes a linear or branched alkyl group having 1-18 carbon atoms which may be substituted with Cl; R₂ denotes a linear or branched alkyl group, alkoxy group or alkoxycarbonyl group having 1-18 carbon atoms; and B denotes —O.CO—, —CO.O—, —OCH₂ or —CH₂O.

6. A device according to claim 6, wherein said pair of substrates are disposed so as to have a spacing therebetween which is sufficiently small so as to release the helical structure of the ferroelectric liquid crystal composition.

7. A device according to claim 5, wherein each substrate has an electrode thereon.

8. A device according to claim 5, wherein each of the substrates is provided with a rubbing treated film.

9. A device according to claim 5, which further comprises means for applying an electric field for switching the aligned state of the ferroelectric liquid crystal molecules, and means for applying an AC electric field to provide an increased tilt angle of the ferroelectric liquid crystal.

10. A device according to claim 5, wherein the mesomorphic compound represented by the formula (I) is one of the following formulas A-1 to A-40:

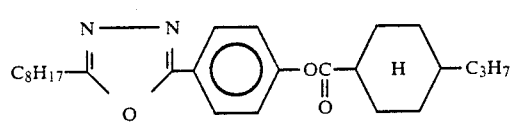 A-1

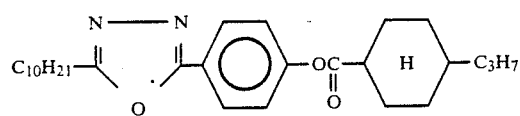 A-2

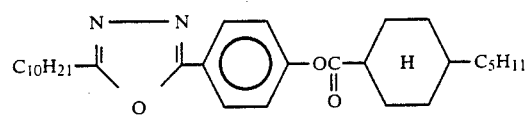 A-3

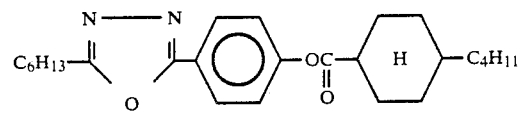 A-4

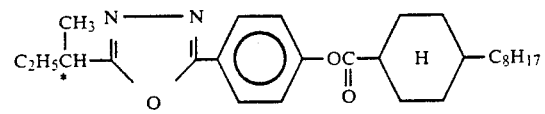 A-5

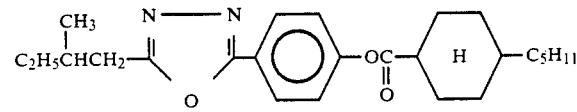 A-6

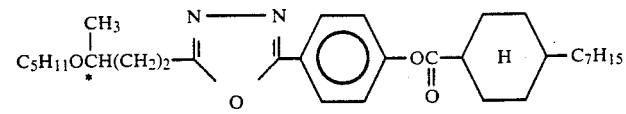 A-7

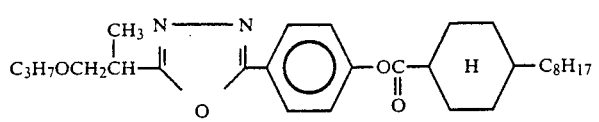
A-8
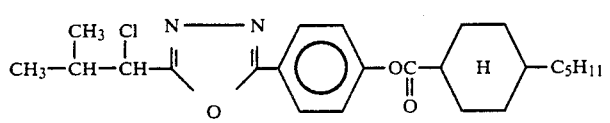
A-9
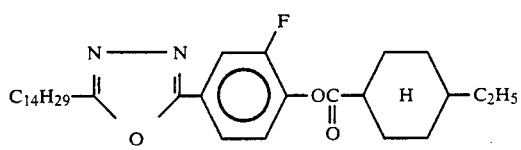
A-10
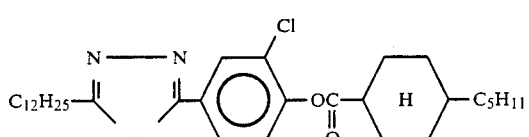
A-11
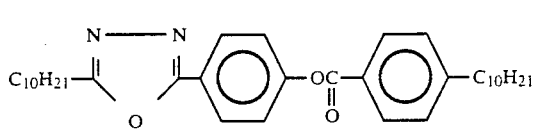
A-12
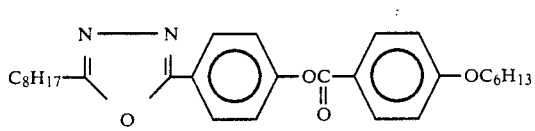
A-13
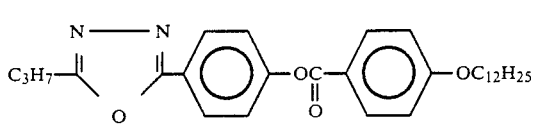
A-14
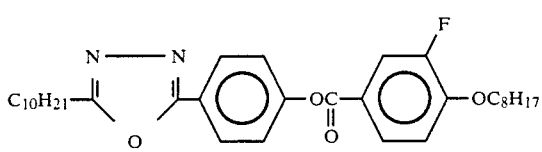
A-15
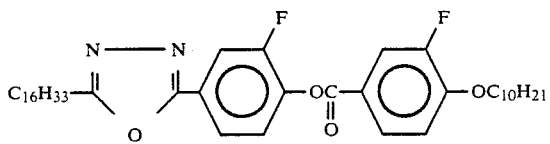
A-16
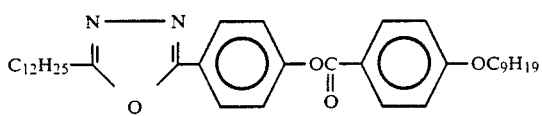
A-17
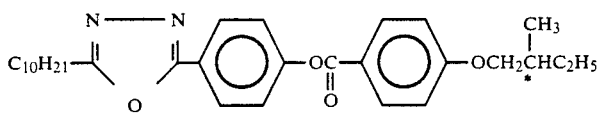
A-18
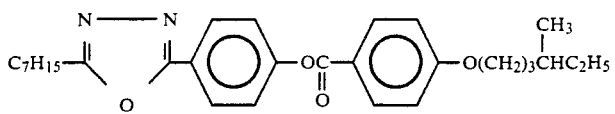
A-19

-continued
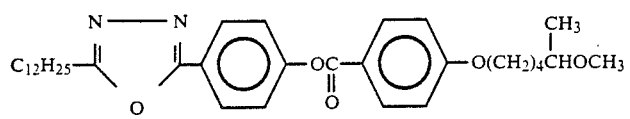 A-20
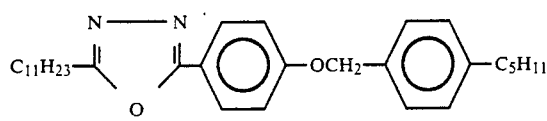 A-21
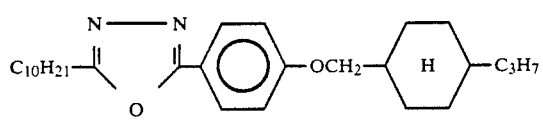 A-22
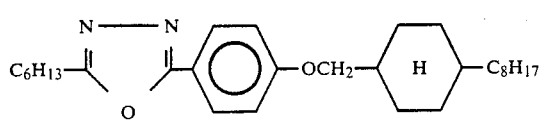 A-23
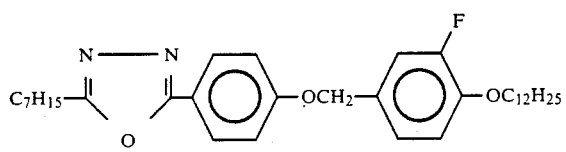 A-24
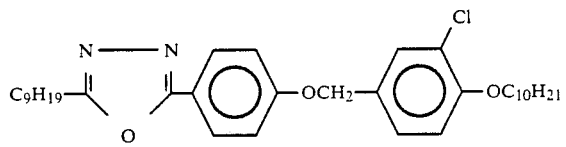 A-25
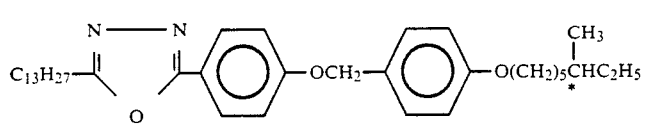 A-26
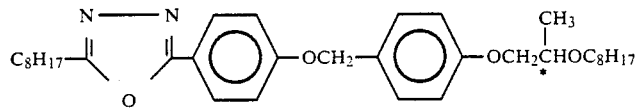 A-27
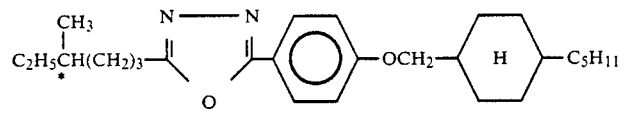 A-28
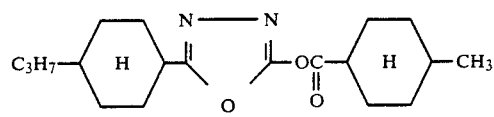 A-29
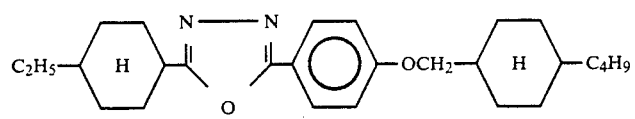 A-30
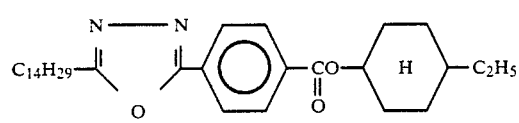 A-31
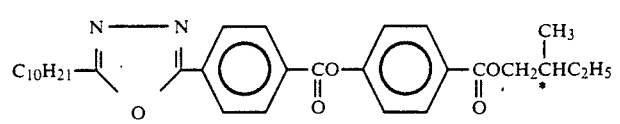 A-32

-continued
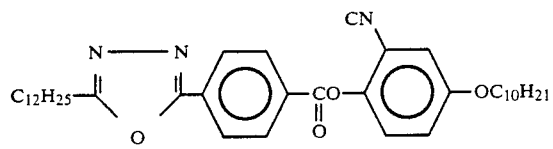
A-33
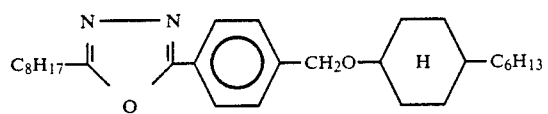
A-34
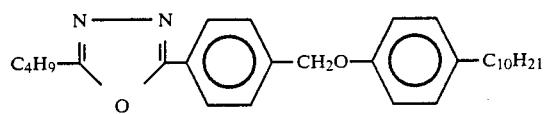
A-35
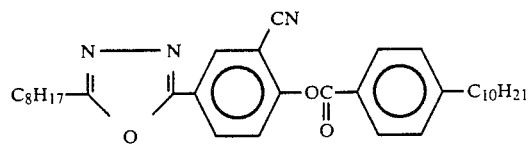
A-36
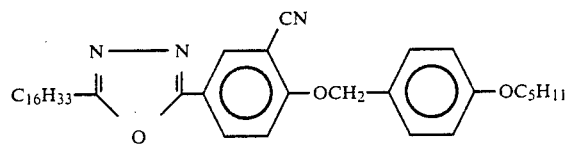
A-37
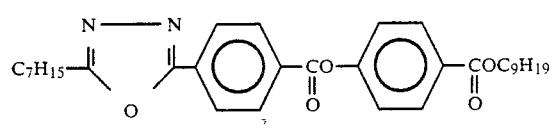
A-38
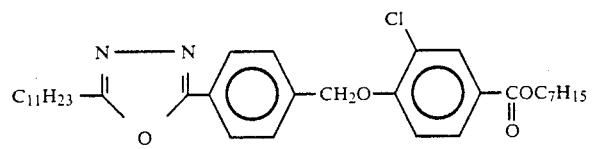
A-39
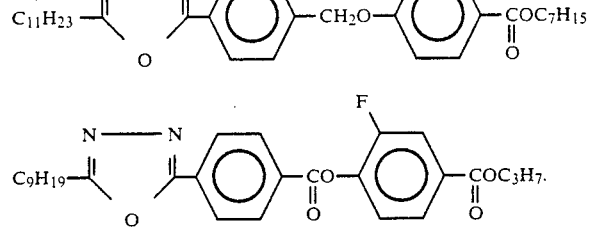
A-40
* * * * *

UNITED STATES PATENT AND TRADEMARK OFFICE
CERTIFICATE OF CORRECTION

PATENT NO. : 5,034,151
DATED : July 23, 1991
INVENTOR(S) : KENJI SHINJO, ET AL.

It is certified that error appears in the above-identified patent and that said Letters Patent is hereby corrected as shown below:

ON THE TITLE PAGE:

IN [56] REFERENCES CITED

Under FOREIGN PATENT DOCUMENTS,
"117014   12/1985   German Democratic Rep." should read
--117014   12/1975   German Democratic Rep.--;

"8808019   10/1988   World Int. Prop. O ... 252/299.61" should be deleted;

| | | | | |
|---|---|---|---|---|
| "245142 | of 1986 | should | --245142 | 10/1986 |
| 246722 | of 1986 | read | 246722 | 11/1986 |
| 246723 | of 1986 | | 246723 | 11/1986 |
| 246724 | of 1986 | | 246724 | 11/1986 |
| 249024 | of 1986 | | 249024 | 11/1986 |
| 249025 | of 1986" | | 249025 | 11/1986--. |

IN [57] ABSTRACT

Page 2, Column 1, Line 3, "denotes" should read --denote--.
Page 2, Column 2, Line 1, "substituted of" should read --substituent--.

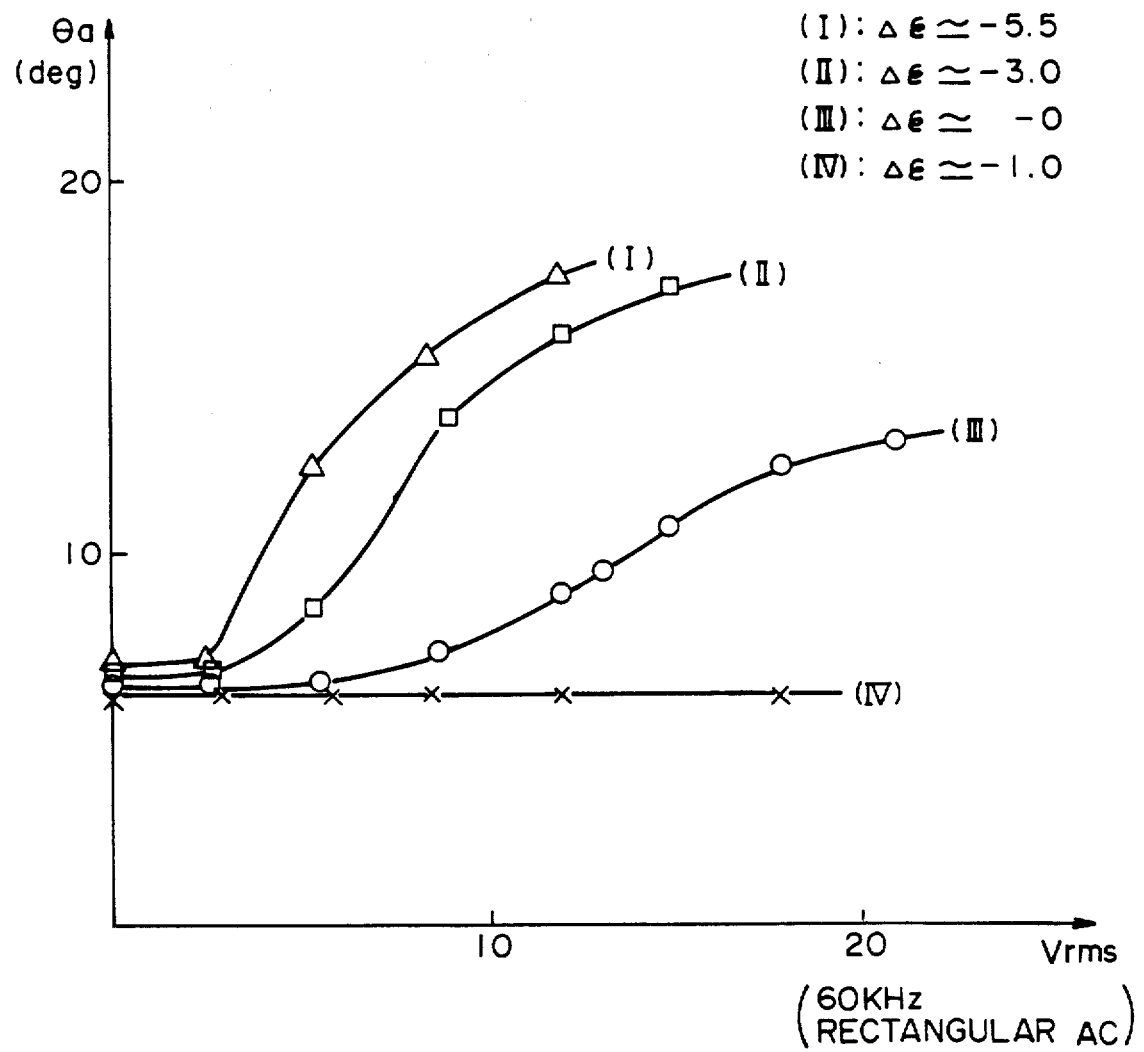

UNITED STATES PATENT AND TRADEMARK OFFICE
CERTIFICATE OF CORRECTION

PATENT NO. : 5,034,151
DATED : July 23, 1991
INVENTOR(S) : KENJI SHINJO, ET AL.

It is certified that error appears in the above-identified patent and that said Letters Patent is hereby corrected as shown below:

COLUMN 1

Line 36, "(director n)" should read --(director ñ)--.
Line 39, "of n)" should read --of ñ)--.
Line 45, "(RAR/u/)" should read --(ū)--.
Line 48, "(RAR/u/)" should read --(ū)--.
Line 54, "(n)," should read --(ñ),--.
Line 57, "(n)" should read --(ñ)--.

COLUMN 2

Line 35, "viscosity τ" should read --viscosity η--.

COLUMN 3

Line 7, "directors n" should read --directors ñ--.

COLUMN 5

Line 2, "denotes" should read --denote--.
Line 5, "substituted" should read --substituent--.

COLUMN 25

Line 20, "compound," should read --compounds,--.

UNITED STATES PATENT AND TRADEMARK OFFICE
CERTIFICATE OF CORRECTION

PATENT NO. : 5,034,151
DATED : July 23, 1991
INVENTOR(S) : KENJI SHINJO, ET AL.

It is certified that error appears in the above-identified patent and that said Letters Patent is hereby corrected as shown below:

COLUMN 44

Change as follows:

| | | |
|---|---|---|
| "CRC/1/" | should | -- ① --. |
| "CRC/2/" | read | -- ② --. |
| "CRC/3/" | | -- ③ --. |
| "CRC/4/" | | -- ④ --. |
| "CRC/5/" | | -- ⑤ --. |
| "CRC/6/" | | -- ⑥ --. |

COLUMN 46

Change as follows:

| | | |
|---|---|---|
| "CRC/7/" | should | -- ⑦ --. |
| "CRC/8/" | read | -- ⑧ --. |
| "CRC/9/" | | -- ⑨ --. |
| "10" | | -- ⑩ --. |
| "11" | | -- ⑪ --. |
| "12" | | -- ⑫ --. |
| "13" | | -- ⑬ --. |
| "14" | | -- ⑭ --. |
| "15" | | -- ⑮ --. |
| "17" | | -- ⑰ --. |
| "18" | | -- ⑱ --. |
| "19" | | -- ⑲ --. |
| "20" | | -- ⑳ --. |

UNITED STATES PATENT AND TRADEMARK OFFICE
CERTIFICATE OF CORRECTION

PATENT NO. : 5,034,151

DATED : July 23, 1991

INVENTOR(S) : KENJI SHINJO, ET AL.

It is certified that error appears in the above-identified patent and that said Letters Patent is hereby corrected as shown below:

COLUMN 48

Change as follows:

| "21" | should | -- ㉑ --. |
|------|--------|-----------|
| "22" | read   | -- ㉒ --. |
| "23" |        | -- ㉓ --. |
| "24" |        | -- ㉔ --. |
| "25" |        | -- ㉕ --. |
| "26" |        | -- ㉖ --. |
| "27" |        | -- ㉗ --. |
| "28" |        | -- ㉘ --. |
| "29" |        | -- ㉙ --. |
| "30" |        | -- ㉚ --. |
| "31" |        | -- ㉛ --. |
| "32" |        | -- ㉜ --. |
| "33" |        | -- ㉝ --. |

COLUMN 50

Change as follows:

| "34" | should | -- ㉞ --. |
|------|--------|-----------|
| "35" | read   | -- ㉟ --. |
| "36" |        | -- ㊱ --. |
| "37" |        | -- ㊲ --. |
| "39" |        | -- ㊳ --. |

UNITED STATES PATENT AND TRADEMARK OFFICE
CERTIFICATE OF CORRECTION

PATENT NO. : 5,034,151

DATED : July 23, 1991

INVENTOR(S) : KENJI SHINJO, ET AL.

It is certified that error appears in the above-identified patent and that said Letters Patent is hereby corrected as shown below:

COLUMN 50

Change as follows:

| "40" | should | -- ⓐ --. |
|------|--------|----------|
| "41" | read   | -- ㊶ --. |
| "42" |        | -- ㊷ --. |
| "43" |        | -- ㊸ --. |
| "44" |        | -- ㊹ --. |
| "45" |        | -- ㊺ --. |
| "46" |        | -- ㊻ --. |

COLUMN 52

Change as follows:

| "47" | should | -- ㊼ --. |
|------|--------|----------|
| "48" | read   | -- ㊽ --. |
| "49" |        | -- ㊾ --. |
| "50" |        | -- ㊿ --. |
| "51" |        | -- ㋑ --. |
| "52" |        | -- ㋒ --. |
| "53" |        | -- ㋓ --. |
| "54" |        | -- ㋔ --. |
| "55" |        | -- ㋕ --. |
| "56" |        | -- ㋖ --. |
| "57" |        | -- ㋗ --. |
| "58" |        | -- ㋘ --. |

UNITED STATES PATENT AND TRADEMARK OFFICE
CERTIFICATE OF CORRECTION

PATENT NO. : 5,034,151

DATED : July 23, 1991

INVENTOR(S) : KENJI SHINJO, ET AL.

It is certified that error appears in the above-identified patent and that said Letters Patent is hereby corrected as shown below:

COLUMN 54

Change as follows:

| | | |
|---|---|---|
| "59" | should | -- ⑤⑨ --. |
| "60" | read | -- ⑥⓪ --. |
| "61" | | -- ⑥① --. |
| "62" | | -- ⑥② --. |
| "63" | | -- ⑥③ --. |
| "64" | | -- ⑥④ --. |
| "65" | | -- ⑥⑤ --. |
| "66" | | -- ⑥⑥ --. |
| "67" | | -- ⑥⑦ --. |
| "68" | | -- ⑥⑧ --. |
| "69" | | -- ⑥⑨ --. |
| "70" | | -- ⑦⓪ --. |

COLUMN 56

Change as follows:

| | | |
|---|---|---|
| "71" | should | -- ⑦① --. |
| "72" | read | -- ⑦② --. |
| "73" | | -- ⑦③ --. |
| "74" | | -- ⑦④ --. |
| "75" | | -- ⑦⑤ --. |
| "76" | | -- ⑦⑥ --. |

UNITED STATES PATENT AND TRADEMARK OFFICE
CERTIFICATE OF CORRECTION

PATENT NO. : 5,034,151
DATED : July 23, 1991
INVENTOR(S) : KENJI SHINJO, ET AL.

It is certified that error appears in the above-identified patent and that said Letters Patent is hereby corrected as shown below:

COLUMN 56

Change as follows:

| "77" | should | -- ⑦ --. |
|------|--------|----------|
| "78" | read   | -- ⑱ --. |
| "79" |        | -- ⑲ --. |
| "80" |        | -- ⑳ --. |
| "81" |        | -- ㉑ --. |
| "83" |        | -- ㉓ --. |
| "84" |        | -- ㉔ --. |

COLUMN 59

Line 1, "4.97 X $10^{-3}$mol)" should read --(4.97 X $10^{-3}$mol)--.
Line 33, "subjected" should read --subjected to--.

COLUMN 60

Line 10, "CRC/10/" should read -- ⑩ --.
Line 12, "CRC/10/" should read -- ⑩ --.
Line 32, "CRC/10/" should read -- ⑩ --.
Line 67, "a of" should read --a $\Delta\varepsilon$--.

COLUMN 62

Line 12, "R ($cm^{-1}$)" should read --IR ($cm^{-1}$)--.
Line 30, "reaction was" should read --reaction mixture was--.
Line 66, "subjected" should read --subjected to--.

UNITED STATES PATENT AND TRADEMARK OFFICE
CERTIFICATE OF CORRECTION

PATENT NO. : 5,034,151
DATED : July 23, 1991
INVENTOR(S) : KENJI SHINJO, ET AL.

It is certified that error appears in the above-identified patent and that said Letters Patent is hereby corrected as shown below:

COLUMN 63

Line 44, "CRC/10/" should read -- ⑩ --.
Line 46, "CRC/10/" should read -- ⑩ --.
Line 66, "CRC/10/" should read -- ⑩ --.

COLUMN 64

Line 18, "subjected" should read --subjected to--.
Line 40, "CRC/1/," should read --①--.
Line 41, "CRC/5/, CRC/6/, CRC/7/ and CRC/9/" should read
        -- ⑤, ⑥, ⑦, and ⑨ --.
Line 43, "CRC/1/" should read --①--.
Line 44, ":CRC/5/  :CRC/6/  :E,crc/7/  :CRC/9/" should
        read --: ⑤ : ⑥ : ⑦ : ⑨ --.
Line 45, ":" (first occurrence) should be deleted.
Line 51, "B-33   80" should read --B-33=80--.

COLUMN 69

Formula A-29,
"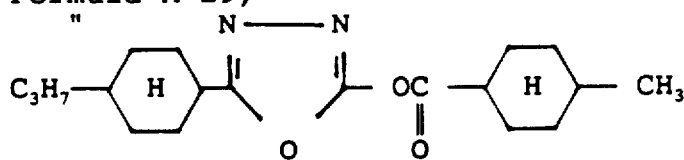"          should read

-- 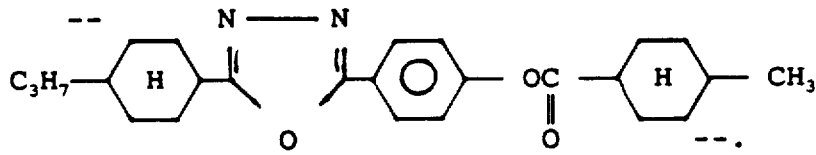 --.

UNITED STATES PATENT AND TRADEMARK OFFICE
CERTIFICATE OF CORRECTION

PATENT NO. : 5,034,151
DATED : July 23, 1991
INVENTOR(S) : KENJI SHINJO, ET AL.

It is certified that error appears in the above-identified patent and that said Letters Patent is hereby corrected as shown below:

COLUMN 74

Line 13, "claim 6," should read --claim 5,--.
Line 14, "are" should read --is--.

Formula A-4,

"      "     should read

-- 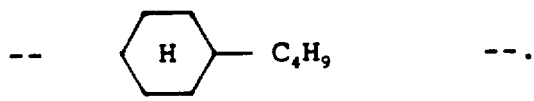     --.

UNITED STATES PATENT AND TRADEMARK OFFICE
CERTIFICATE OF CORRECTION

PATENT NO. : 5,034,151
DATED : July 23, 1991
INVENTOR(S) : KENJI SHINJO, ET AL.

It is certified that error appears in the above-identified patent and that said Letters Patent is hereby corrected as shown below:

<u>COLUMN 77</u>

Formula A-29,

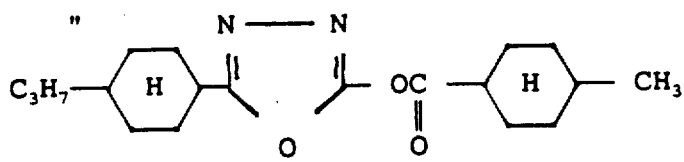

should read

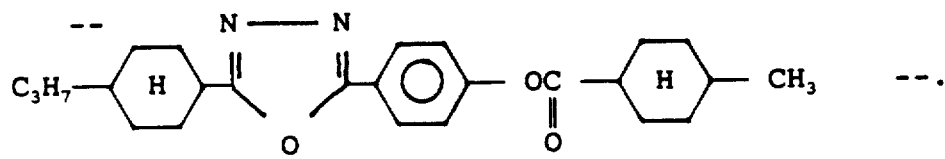

--.

Signed and Sealed this

Twenty-sixth Day of April, 1994

Attest:

BRUCE LEHMAN

Attesting Officer      Commissioner of Patents and Trademarks